US010668014B2

(12) United States Patent
Kovarik et al.

(10) Patent No.: US 10,668,014 B2
(45) Date of Patent: *Jun. 2, 2020

(54) METHOD AND SYSTEM FOR PREVENTING SORE THROAT IN HUMANS

(71) Applicants: Joseph E. Kovarik, Englewood, CO (US); Katherine Rose Kovarik, Englewood, CO (US)

(72) Inventors: Joseph E. Kovarik, Englewood, CO (US); Katherine Rose Kovarik, Englewood, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/136,950

(22) Filed: Sep. 20, 2018

(65) Prior Publication Data
US 2019/0015322 A1 Jan. 17, 2019

Related U.S. Application Data

(63) Continuation of application No. 15/385,278, filed on Dec. 20, 2016, now Pat. No. 10,085,938, which is a (Continued)

(51) Int. Cl.
*A61K 9/00* (2006.01)
*A61F 5/56* (2006.01)
(Continued)

(52) U.S. Cl.
CPC ............... *A61K 9/006* (2013.01); *A61F 5/566* (2013.01); *A61K 9/7007* (2013.01);
(Continued)

(58) Field of Classification Search
CPC .... A61K 9/006; A61K 9/7007; A61K 31/047; A61K 35/744; A61K 49/0045;
(Continued)

(56) References Cited

U.S. PATENT DOCUMENTS 3,178,341 A 4/1965 Hamill et al.
4,136,145 A 1/1979 Fuchs et al.
(Continued)

FOREIGN PATENT DOCUMENTS

WO PCT/US2007/023166 7/2008

OTHER PUBLICATIONS

Oral cavity: retrieved form https://histology.medicine.umich.edu/resources/oral-cavity. Retrieved on Nov. 20, 2019.*

*Primary Examiner* — Hong Yu
(74) *Attorney, Agent, or Firm* — Sheridan Ross P.C.

(57) ABSTRACT

A method and system to prevent sore throat infections in humans includes the administration of an active ingredient to a site on the mucus membranes of the throat of a human that inhibits adherence and promotes desorption of *S. pyogenes* to soft tissue surfaces, such as the pharyngeal and oral mucosa of a human. A mucoadhesive strip having a surface topography that resists bioadhesion of undesired bacteria that are typically present in a human's mouth is preferably employed and that has one or more encapsulated agents selected from the group consisting of an antibiotic; lactic acid bacteria; *S. pyogenes* modified by a CRISPR-Cas system to reduce one or more virulence factors; and a breath mint solution.

17 Claims, 10 Drawing Sheets

Related U.S. Application Data continuation-in-part of application No. 14/752,192, filed on Jun. 26, 2015, now Pat. No. 9,549,842, which is a continuation-in-part of application No. 14/225,503, filed on Mar. 26, 2014, now Pat. No. 9,445,936, which is a continuation of application No. 13/368,052, filed on Feb. 6, 2012, now Pat. No. 8,701,671, said application No. 15/385,278 is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, said application No. 15/385,278 is a continuation-in-part of application No. 15/228,454, filed on Aug. 4, 2016, now Pat. No. 9,585,920, and a continuation-in-part of application No. 14/611,458, filed on Feb. 2, 2015, now Pat. No. 10,398,209, which is a continuation-in-part of application No. 14/502,097, filed on Sep. 30, 2014, now Pat. No. 9,010,340, which is a continuation of application No. 14/307,651, filed on Jun. 18, 2014, now Pat. No. 8,936,030, which is a continuation-in-part of application No. 14/079,054, filed on Nov. 13, 2013, now Pat. No. 8,757,173, which is a continuation of application No. 13/425,913, filed on Mar. 21, 2012, now Pat. No. 8,584,685.

(60) Provisional application No. 62/387,404, filed on Dec. 24, 2015, provisional application No. 61/439,652, filed on Feb. 4, 2011, provisional application No. 61/556,023, filed on Nov. 4, 2011, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 62/387,405, filed on Dec. 24, 2015, provisional application No. 62/274,550, filed on Jan. 4, 2016, provisional application No. 62/275,341, filed on Jan. 6, 2016, provisional application No. 61/467,767, filed on Mar. 25, 2011.

(51) Int. Cl.
*A61K 35/741* (2015.01)
*A61K 45/06* (2006.01)
*A61K 35/74* (2015.01)
*A61K 31/047* (2006.01)
*A61K 49/00* (2006.01)
*A61K 35/744* (2015.01)
*A61K 9/70* (2006.01)

(52) U.S. Cl.
CPC ............ *A61K 31/047* (2013.01); *A61K 35/74* (2013.01); *A61K 35/741* (2013.01); *A61K 35/744* (2013.01); *A61K 45/06* (2013.01); *A61K 49/0045* (2013.01); *A61K 49/0069* (2013.01)

(58) Field of Classification Search
CPC .... A61K 49/0069; A61K 35/74; A61K 45/06; A61K 35/741; A61F 5/566
See application file for complete search history.

(56) References Cited

U.S. PATENT DOCUMENTS

| | | |
|---|---|---|
| 4,136,162 A | 1/1979 | Fuchs et al. |
| 4,568,639 A | 2/1986 | Lew |
| 4,687,841 A | 8/1987 | Spilburg et al. |
| 4,720,486 A | 1/1988 | Spilburg et al. |
| 4,849,246 A | 7/1989 | Schmidt |
| 4,995,555 A | 2/1991 | Woodruff |
| 5,081,158 A * | 1/1992 | Pomerantz ............ A61K 9/006 106/168.01 |
| 5,166,233 A | 11/1992 | Kuroya et al. |
| 5,190,053 A | 3/1993 | Meer et al. |
| 5,277,877 A | 1/1994 | Jeffrey et al. |
| 5,578,315 A | 11/1996 | Chien et al. |
| 5,585,098 A | 12/1996 | Coleman |
| 5,614,501 A | 3/1997 | Richards |
| 6,072,100 A | 6/2000 | Mooney et al. |
| 6,284,235 B1 | 9/2001 | Foreman et al. |
| 6,287,610 B1 | 9/2001 | Bowling et al. |
| 6,502,574 B2 | 1/2003 | Stevens et al. |
| 6,552,024 B1 | 4/2003 | Chen |
| 6,569,474 B2 | 5/2003 | Clayton et al. |
| 6,722,577 B2 | 4/2004 | Dobyns, III |
| 6,748,951 B1 | 6/2004 | Schmidt |
| 6,923,981 B2 | 8/2005 | Leung |
| 7,138,135 B2 | 11/2006 | Chen |
| 7,267,975 B2 | 9/2007 | Strobel et al. |
| 7,276,246 B2 | 10/2007 | Zhang |
| 7,353,194 B1 | 4/2008 | Kerker et al. |
| 7,441,559 B2 | 10/2008 | Nelson |
| 7,470,397 B2 | 12/2008 | Meathrel et al. |
| 7,500,484 B2 | 3/2009 | Nelson |
| 7,540,432 B2 | 6/2009 | Majerowski et al. |
| 7,566,310 B2 | 7/2009 | Badr et al. |
| 7,632,525 B2 | 12/2009 | Dodds et al. |
| 7,648,712 B2 | 1/2010 | Bess et al. |
| 7,650,848 B2 | 1/2010 | Brennan et al. |
| 7,820,420 B2 | 10/2010 | Whitlock |
| 7,824,588 B2 | 11/2010 | Yang et al. |
| 7,845,356 B2 | 12/2010 | Paraschac et al. |
| 7,862,808 B2 | 1/2011 | Isolauri et al. |
| 7,984,714 B2 | 7/2011 | Hausmann et al. |
| 8,034,606 B2 | 10/2011 | Park et al. |
| 8,197,872 B2 | 6/2012 | Mills et al. |
| 8,349,313 B2 | 1/2013 | Smith et al. |
| 8,420,074 B2 | 4/2013 | Rehberger et al. |
| 8,454,729 B2 | 6/2013 | Mittelmark et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,758,764 B2 | 6/2014 | Masignani et al. |
| 8,815,538 B2 | 8/2014 | Lanzalaco et al. |
| 8,951,775 B2 | 2/2015 | Castiel |
| 9,011,834 B1 | 4/2015 | McKenzie et al. |
| 9,017,718 B2 | 4/2015 | Tan |
| 9,028,841 B2 | 5/2015 | Henn et al. |
| 9,056,912 B2 | 6/2015 | Grandi |
| 9,095,704 B2 | 8/2015 | McGuire |
| 9,131,884 B2 | 9/2015 | Holmes |
| 9,149,429 B2 | 10/2015 | Kovacs et al. |
| 9,234,204 B2 | 1/2016 | Qvit-Raz et al. |
| 9,288,981 B2 | 3/2016 | Gandhi et al. |
| 9,445,936 B2 | 9/2016 | Kovarik |
| 9,549,842 B2 | 1/2017 | Kovarik |
| 10,085,938 B2 * | 10/2018 | Kovarik .................. A61F 5/566 |
| 2003/0206995 A1 | 11/2003 | Bowling et al. |
| 2004/0053352 A1 | 3/2004 | Ouyang et al. |
| 2004/0115223 A1 | 6/2004 | Follansbee |
| 2004/0142463 A1 | 7/2004 | Walker et al. |
| 2004/0166501 A1 | 8/2004 | Azimzai et al. |
| 2005/0159637 A9 | 1/2005 | Nelson et al. |
| 2005/0118655 A1 | 6/2005 | Weinstock et al. |
| 2005/0260544 A1 | 11/2005 | Jones et al. |
| 2006/0188813 A1 | 8/2006 | Shimada |
| 2006/0207721 A1 | 9/2006 | Slominski et al. |

(56) References Cited

U.S. PATENT DOCUMENTS

| | | |
|---|---|---|
| 2006/0252087 A1 | 11/2006 | Tang et al. |
| 2007/0054008 A1 | 3/2007 | Clayton et al. |
| 2007/0057086 A1 | 3/2007 | Van Kippersluis |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0202057 A1 | 8/2007 | Fankhauser et al. |
| 2007/0207955 A1 | 9/2007 | Tanihara et al. |
| 2007/0218114 A1 | 9/2007 | Duggan et al. |
| 2007/0231923 A1 | 10/2007 | Cumberland et al. |
| 2008/0075825 A1 | 3/2008 | Fuisz et al. |
| 2008/0112983 A1 | 5/2008 | Bufe et al. |
| 2008/0286210 A1 | 11/2008 | He |
| 2008/0305089 A1 | 12/2008 | Bufe et al. |
| 2009/0098192 A1 | 4/2009 | Fuisz |
| 2009/0205083 A1 | 8/2009 | Gupta et al. |
| 2010/0029832 A1 | 2/2010 | Pinnavaia et al. |
| 2010/0247644 A1 | 9/2010 | Domb |
| 2010/0260720 A1 | 10/2010 | Sprenger |
| 2011/0009834 A1 | 1/2011 | Asmussen |
| 2011/0033542 A1 | 2/2011 | Myers et al. |
| 2011/0250626 A1 | 10/2011 | Williams et al. |
| 2012/0027786 A1 | 2/2012 | Gupta |
| 2012/0029832 A1 | 2/2012 | Dodgson |
| 2012/0039806 A1 | 2/2012 | Lahoud et al. |
| 2012/0128597 A1 | 5/2012 | Peters et al. |
| 2012/0142548 A1 | 6/2012 | Corsi et al. |
| 2012/0276143 A1 | 11/2012 | O3 Mahony et al. |
| 2012/0276525 A1 | 11/2012 | Kovarik et al. |
| 2013/0059815 A1 | 3/2013 | Fournell et al. |
| 2013/0157876 A1 | 6/2013 | Lynch et al. |
| 2013/0259834 A1 | 10/2013 | Klaenhammer et al. |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0238411 A1 | 8/2014 | Kovarik |
| 2014/0255351 A1 | 9/2014 | Berstad et al. |
| 2014/0349405 A1 | 11/2014 | Sontheimer et al. |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0166641 A1 | 6/2015 | Goodman |
| 2015/0190435 A1 | 7/2015 | Henn et al. |
| 2015/0216917 A1 | 8/2015 | Jones |
| 2015/0224072 A1 | 8/2015 | Pellikaan |
| 2015/0290026 A1 | 10/2015 | Kovarik |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0168594 A1 | 6/2016 | Zhang et al. |
| 2016/0151427 A1 | 8/2016 | Whitlock et al. |
| 2016/0271189 A1 | 9/2016 | Cutcliffe |
| 2016/0314281 A1 | 10/2016 | Apte |
| 2017/0100329 A1 | 4/2017 | Kovarik |

\* cited by examiner

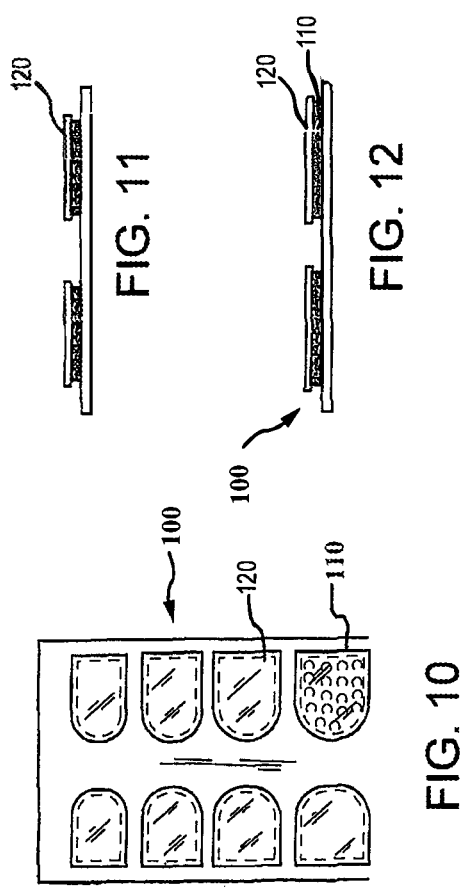

METHOD AND SYSTEM FOR PREVENTING SORE THROAT IN HUMANS

RELATED APPLICATIONS

This application is a continuation of U.S. patent application Ser. No. 15/385,278, filed Dec. 20, 2016 (now U.S. Pat. Ser. No. 10/085,938, issues Oct. 2, 2018), which seeks priority from U.S. Provisional Patent Application Ser. No. 62/387,404.

This application is a continuation-in-part application of U.S. patent application Ser. No. 14/752,192 filed Jun. 26, 2015 (now U.S. Pat. No. 9,549,842, issued Jan. 24, 2017), which is a continuation-in-part application of U.S. patent application Ser. No. 14/225,503 filed Mar. 26, 2014, (now issued U.S. Pat. No. 9,445,936, issued Sep. 20, 2016), which is a continuation of U.S. patent application Ser. No. 13/367,052, filed Feb. 6, 2012 (now issued U.S. Pat. No. 8,701,671, issuing on Apr. 22, 2014), which claims priority of U.S. Provisional Patent Application Ser. No. 61/439,652, filed on Feb. 4, 2011 and U.S. Provisional Patent Application Ser. No. 61/556,023, filed on Nov. 4, 2011.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016), which is a continuation-in-part application of U.S. patent application Ser. No. 14/574,517, filed on Dec. 18, 2014 (now issued U.S. Pat. No. 9,408,880, issuing on Aug. 9, 2016), which claims priority of U.S. Provisional Patent Application Ser. Nos. 62/072,476, filed on Oct. 30, 2014; 62/053,926, filed on Sep. 23, 2014; 62/014,855, filed on Jun. 20, 2014; and 61/919,297, filed on Dec. 20, 2013.

This application is also a continuation-in-part application of U.S. patent application Ser. No. 15/228,454, filed Aug. 4, 2016 (now U.S. Pat. No. 9,585,920, issued Mar. 7, 2017).

This application claims priority of U.S. Provisional Patent Application Ser. Nos. 62/387,405, filed Dec. 24, 2015; 62/274,550, filed Jan. 5, 2016; and 62/275,341, filed Jan. 6, 2016.

This application is also a continuation-in-part application of U.S. patent application Ser. No. 14/611,458, filed Feb. 2, 2015, which is a continuation-in-part application of U.S. patent application Ser. No. 14/502,097, filed Sep. 30, 2014 (now issued U.S. Pat. No. 9,010,340, issuing on Apr. 21, 2015), which is a continuation of U.S. patent application Ser. No. 14,307,651, filed on Jun. 18, 2014 (now issued U.S. Pat. No. 8,936,030, issuing Jan. 20, 2015), which is a continuation-in-part application of U.S. patent application Ser. No. 14/079,054, filed Nov. 13, 2013 (now issued U.S. Pat. No. 8,757,173, issuing on Jun. 24, 2014), which is a continuation of U.S. patent application Ser. No. 13/425,913. filed Mar. 21, 2012 (now issued U.S. Pat. No. 8,584,685, issuing on Nov. 19, 2013), and claims priority of U.S. Provisional Patent Application Ser. No. 61/467,767, filed Mar. 25, 2011.

The entire disclosure of the prior applications are considered to be part of the disclosure of the accompanying application and are hereby incorporated by reference

FIELD OF THE INVENTION

The present invention is directed to a method and system to prevent sore throat infections in humans.

BACKGROUND OF THE INVENTION

The number of people with sore throats in the United States that seek medical attention is an estimated 120 million visits per year. Approximately 12 to 25 percent of those individuals have positive strep cultures. Far more individuals than those diagnosed with strep throat are placed on antibiotics because there are no other available treatments. *Streptococcus* is one of the most frequent causes for visits to the doctor's office in the United States. It is also one of the most frequent reasons for antibiotic use. *Streptococcus* is also a concern due to the development of not only throat infections, but also due to the other sequella of the infection, namely rheumatoid heart disease. This is where the organism invades the blood stream and causes vegetations on the heart valves.

*Streptococcus* is a genus of spherical, Gram-positive bacteria that are known to be the primary cause of throat infections in humans. Streptococcal sore throat, or strep throat as it is more commonly called, is an infection of the mucous membranes lining the pharynx. Sometimes the tonsils are also infected (tonsillitis). *Streptococcus pyogenes*, a group A *Streptococcus* (GAS), is the causative agent in Group A for Streptococcal infections including strep throat, acute rheumatic fever, scarlet fever and acute glomerulonephritis (inflation of the glomeruli). The reason why *S. pyogenes* sometimes causes disease is not entirely understood, but both bacterial virulence factors and host factors are thought to contribute. The microbiota is one such host factor that needs further investigation. Attachment to epithelial cells is the crucial initial step of colonization because non-adherent GAS is removed by mucus and saliva flow.

Conventional therapy for *S. pyogenes* infections has mainly consisted of treatment with antibiotics such as penicillin and tetracycline. The large numbers of people that are prescribed antibiotics for this illness helps to increase the incidence of resistant bacteria as observed in rising levels of antibiotic resistant infections in the public. Antibiotics that were once almost universally effective against these infections are now approximately 70 to 80% effective. Moreover, antibiotics such as penicillin and tetracycline, exhibit broad spectrum antimicrobial activity. Thus, treatment with these antibiotics tends to kill not only *S. pyogenes* but a number of other bacterial species, some of which may actually be beneficial to the body. Although *S. pyogenes* may be treated using antibiotics, a prophylactic vaccine to prevent the onset of disease has been desired. Efforts to develop such a vaccine have been ongoing for many decades, but yet, to date, there are no GAS vaccines available to the public.

There is a long felt but unsolved need for a preventative treatment for sore throat and especially one that does not present the problems associated with the use of antibiotics.

SUMMARY OF THE INVENTION

Various embodiments of the present invention are directed to a method and system that a person can employ when they first fear they may be coming down with a sore throat or just prior to full blown feelings of a sore throat. The application of a strip to the soft palate region of their throat is believed to eliminate the chances they will experience and suffer a sore throat. This is because the strips as described herein are effective in diminishing, if not precluding or prohibiting the growth of particular bacteria, especially *S. pyogenes*, which is largely responsible for sore throats. The provision on or in such strip of certain sugars, including xylitol but also certain other oligosaccharides, in concert with other structural features of the surface of such strip that make bacteria avoid such surface, because they cannot adhere well thereto, prevents the continued progression of a sore throat that a person would otherwise experience. Moreover, in certain other embodiments, coaggregation of *S. pyogenes* is achieved by populating the strip with an effective amount of preferred lactic acid bacteria (LAB) that are able to coaggregate specifically with *Streptococcus pyogenes*. Coaggregation is understood in the sense of the invention in particular as adhesion, interaction, binding, specific binding, affinity or interaction and characterizes in particular the ability of the preferred microorganisms to form agglomerates with *Streptococcus pyogenes*. *S. pyogenes* has evolved a number of different types of molecules, referred to as "adherens," on its surface which can very tightly stick to one or more molecules that are part of the host's various surfaces. Few strains of *Lactobacillus* are capable of preventing the binding of *Streptococcus pyogenes* (group A streptococci, also referred to as GAS) GAS to human cell lines. The *Lactobacillus* strains compete with GAS for surface structures on the cells and thus prevent GAS from invading the host cells. Adhesion of *Streptococcus pyogenes* to the host cell is the first step in pathogenesis, and the invasion process into the host cells takes place in very short order. The early use of therapeutic agents for prevention and treatment are of crucial importance to reduce the total GAS microbe count and to efficiently prevent the binding, i.e., invasion of *Streptococcus pyogenes*, is one objective of the present invention. Use of certain LAB in various aspects of the present invention preferably involves the following microorganisms deposited with the German Collection for Microorganisms and Cell Cultures under the code numbers DSM 25972, DSM 25987, DSM 25988, DSM 25989, DSM 25973.

One objective is to decrease the colonization of the oropharynx, and therefore decrease symptoms of the sore inflamed throat and ultimately decrease the need for antibiotics. In certain embodiments of the present invention, conjugated oligosaccharides are employed to specifically inhibit the adherence of *S. pyogenes* to pharyngeal and oral mucosal cells. In the first stages of infection, bacterial adhesins, adhesive molecules on the surface of bacteria, bind to receptor materials on the host cell membrane. Thus, certain embodiments of the present invention are directed to defeating the adherence of *S. pyogenes* to a person's oral tissue in a manner that results in avoiding a sore throat.

Pathogenic bacteria display various levels of host specificity or tropism. While many bacteria can infect a wide range of hosts, certain bacteria have strict host selectivity for humans as obligate human pathogens. Host specificity of bacterial pathogens is determined by multiple molecular interactions between the pathogens and their hosts. A number of bacteria are highly adapted to the human environment and display strict host selectivity for humans, including *Haemophilus influenzae*, *Helicobacter pylori*, *Neisseria gonorrhoeae*, *Neisseria meningitidis*, *Mycobacterium leprae*, *Salmonella Typhi*, *Streptococcus pneumoniae*, *Streptococcus pyogenes*, *Vibrio cholerae* and *Treponema pallidum*. Hereinafter these bacteria will be referred to as human-specific pathogens. The cause of strep throat, *Streptococcus pyogenes*, exhibits tissue tropism, i.e. it is virtually found only in humans. One aspect of the present invention, described in detail with respect to sore throat infections but not to be intended to be so limited, is the modification of human specific pathogens to alter or destroy their respective virulence factors, preferably by employing CRISPR-Cas systems, and in so doing, alleviating diseases caused by such microbes without the threat of undesired consequences stemming from a more global and universal modification of bacteria serving other beneficial functions in our environment. In certain embodiments CRISPR-Cas is employed to silence or to delete certain virulence factors of microbes, specifically the virulence factors of *S. pyogenes*, and especially adhesions involved in interspecies coaggregation.

To comply with appropriate written description and enablement requirements and to provide sufficient guidance in how one of skill in the art can make and use the various and numerous embodiments of the present invention, incorporated herein in their entireties are the following, generally directed to *S. pyogenes*: U.S. Pat. No. 5,583,765 to Stolle et. al.; U.S. Pat. No. 5,585,098 to Coleman; U.S. Pat. No. 9,056,912 to Grandi; U.S. Pat. No. 9,131,884 to Holmes; US Pat. Publication No. 2014/0065218 to Lang et. al; PCT/US2007/023166 to Mitteness; 2015/0224072 to Pellikaan; U.S. Pat. No. 9,095,704 to McGuire; 2015/0290026 to Kovarik; U.S. Pat. No. 6,552,024 to Chen; 2003/015656 to Jackson et. al.; and 2005/0260544 to Jones et. al.

Various embodiments of the present invention relate to an improved method and system of inhibiting adherence, and thus promoting desorption of *S. pyogenes* to soft tissue surfaces, such as the pharyngeal and oral mucosa of a human, by treating these areas with one or more of the embodiments described herein directed to a mucoadhesive strip. Particular embodiments are directed to oral strips having a surface topography that resists bioadhesion of undesired bacteria that are typically present in a human's mouth. The strips preferably have a surface that is anti-microbial in nature, such that such strips assist in reducing the surface area in the mouth where noxious odors may arise due to the proliferation of foul smelling agents produced by bacteria that can survive in one's mouth.

Thus, one aspect of the present invention is directed to the novel combination of a specifically surface structured bio-adhesively attachable, and in a preferred embodiment, dissolvable, strip of material that persists in the mouth for at least one hour and preferably at least about 3 hours, so as to reside on the tissue of the throat where *S. pyogenes* would otherwise reside, specifically the soft palate and thus reduce the occurrence of sore throat. The ability to defeat the proliferation of bacteria, including but not limited to *S. pyogenes*, in a person's mouth can significantly decrease the occurrence of so-called "morning breath".

Certain embodiments entail the use of a specially textured surface, either one both or at least the outer side of an adhesive strip (the side facing away from the mucosal tissue to which it is attached) that has anti-microbial characteristics. In one such embodiment, the surface topography is such that it resists bioadhesion of undesired bacteria that are typically present in a human's mouth. Such a surface may comprise a layer or coating that comprises a pattern defined by a plurality of spaced apart features attached to or projected into a base surface, with a plurality of features each having at least one microscale dimension and having at least one neighboring feature having a substantially different geometry, and having an average spacing between adjacent ones of said features of between 0.5 and 5 .mu.m. Incorporated herein by this reference is U.S. Pat. No. 7,650,848 to address written description and enablement issues regarding the use of suitable textures and surfaces that may be employed. Thus, preferred embodiments include strips that have a surface upon which bacteria do not like to grow, in particular, surfaces having a surface texture and/or pattern that faces away from the mucosal contacting side of the strip and that reduces the number of bacteria that would normally occupy such surface area of the mucosal membrane where the patch/strip no adhered thereto, creates a surface upon which bacteria do not like to grow. Exemplary surfaces that can be employed for such purpose include those in FIG. 2(a-d).

Certain embodiments of the patch (or strip as alternatively referred to herein) have overall geometries particularly suited for the individual's mouth and are customizable therefore. As such, perforated tear lines such that smaller sizes can be fashioned easily. Other geometries of strips are such that they limit common "gag reflexes" of a person. Particular strips are designed so as to also extend over not only a majority of the soft palate region, but also over the hard palate, so as to further reduce the incidence of gag reflexes being triggered. Certain embodiments have toxic substances associated with the surface of the strips, thereby killing certain undesired bacteria in the mouth.

Certain other embodiments comprise bioluminescent strips to facilitate a user's ability to view (in a mirror) the correct placement of the strips in one's throat. Bioluminescence is a type of chemiluminescence and in certain embodiments, a catalytic protein increases the efficiency of chemiluminescent reaction such that a bioluminescent protein is determined by detecting the presence of luminescence. Bioluminescent compounds that may be employed in the present invention embodiments include luciferin, luciferase and aequorin. Other embodiments employ differences in visual appearance to determine whether a patch is placed properly; whether certain desired or undesired bacteria are present in the mouth, etc, and such effective means for determining the same include a film, coating or patch that includes one or more of the following characteristics: reflectance, retroreflectance, fluorescence, photoluminescent light transmission, color, tinting strength, and whiteness. Certain embodiments also assist in the detection of whether a person has a certain medical condition, such as strep throat. Thus, in one embodiment, the patch changes color, expresses bioluminescence, etc. if there is strep bacteria present in a predetermined amount. Incorporated herein by this reference for written description purposes in this regard is U.S. Pat. Publication No. 20110250626 to Williams, et al.

Certain other embodiments include strips with compounds residing thereon to facilitate the growth of desired bacteria, such as those deemed beneficial or at least not detrimental to a person's health.

Another aspect of the present invention includes the ability to load or impregnate the mucosal strips with any number of active agents to achieve other desirable aspects, such as breath freshening; administration of particular vitamins, medicinal components, salving of mouth sores, short or long term medication through buccal and mucosal tissues, but especially certain modified bacteria, such as *S. pyogenes*, or LAB as described herein, to lessen the chances of a sore throat infection.

The particular dimensions, thickness, size, area surface texture, flexibility, adhesive characteristics, flavoring and taste, composition (e.g. in terms of medicine, vitamins, nutraceuticals, etc.) for a particular strip can be adjusted as one of skill in the art will appreciate. In one embodiment, and unlike most presently available breath strips (e.g. such as Listerine breath strips) the strips employed in the present invention are both thicker, so as to provide more structural integrity to soft palate tissues upon which such strips adhere, and also have more long term (from at least about 5 minutes to several hours), preferably for at least about 3 hours, more preferably at least about 5 hours and most preferably at least about 6 or more hours—roughly equating to the period of time of a person's sleep Moreover, in preferred embodiments the mucosal strips are designed to adhere well with each other when placed on palate tissue so that layering of the strips can be accomplished so as to custom build a desired thickness of the strips over tissue to be covered.

The area of tissue to be covered can be addressed by either having the person provide strips side-by-side to cover the area; by having certain tissue areas provided with thicker ultimate strip depth than other areas (e.g. providing for the option of stiffening certain palate soft tissue more than directly adjacent tissue), and even providing strips having different characteristics in terms of a variety of factors, such as taste, composition, adherence or dissolvability characteristics, area, shape, thickness, flavor, duration of flexibility characteristics, etc. In some embodiments, films of desired thickness and having desired properties in terms of dissolving rate, flexibility, provision of stiffness over time, adhesion duration, ability to cause reversible contraction of soft palate tissue.

While in some embodiments standard sized strips of material may be available such that a person can layer, place side-by-side, orient distinctly, etc. strips of appropriately selected strips, on other embodiments, custom strips or films having particular shapes, such as one that covers the particular area of that particular person's soft palate tissue region, is contemplated. As disclosed herein below, strips are referred alternatively to oral films, mucosal films, etc.

Oral films having desired duration of adhesion and freedom from an adverse feeling in the oral cavity on use are selected that adhere to the particular regions of a person's soft palate.

Reference herein to a strip is to any soluble prolonged release presentation of the composition which is conformable and is adapted to lie in a subject's mouth without causing obstruction or interfering with breathing, talking or swallowing or the like, or to conform to the surface of a subjects open skin or wound. Preferably the strip comprises a flexible film or the like. In use, the strip to be placed in a subject's mouth is intended to be placed at the back of the throat. Preferably the strip (or strips, whether layered, certain portions more dissolvable than others, etc.) are positioned on a person's soft palate. This can be achieved via a person's fingers or through the use of an applicator (otherwise described and illustrated.) The strip is particularly suited to delivery of ingredients by delivery to the mucosa of the throat, in particular at the soft tissue in the pharyngeal region of the back of the throat, to keep the pharyngeal membranes moist and lubricated.

The strip is conformed as a relatively thin planar structure to facilitate desired rates of inter-oral dissolution. For example, in certain embodiments, a single strip may be preferably no more than about 150 micron thick, more preferably in the range 100-400 micron thick, and in other embodiments may be over 500 microns in thickness. In other embodiments, however, the ability to layer strips on top of one another provides for the manufacture and availability of strips of more traditional thickness, such as those for example of the breath strips of Listerine, etc. The strip may be of any suitable shape, for example being square or rectangular for ease of storage, placement, distribution in packages, but is preferably generally planar and approximately 0.5 to 2 cm in length and breadth.

In certain embodiments, the strip is manufactured from a material which is soluble within the subject's mouth under the action of saliva and oral enzymes, or under the action of tissue fluids. In other embodiments, however, the strip is made so as not to dissolve and thus, is repeatedly applied to a person's soft palate.

A reusable device that adds the requisite structure to the particular soft palate tissue can have appropriate adhesive integral or added as needed to remain in a desired position. The customization of such a strip in terms of shape, size, characteristics regarding flavor, thickness, adhesive qualities etc. are within the present scope of the invention.

In certain embodiments, the base material for the strip is any suitable soluble solid material, which term includes gel-like and other materials which are sufficiently solid to enable the strip to be conformed to its desired shape. In particular, a carrier or base material of the strip may comprise a soluble gel material, and is for example based upon on an organic gel, which could for example be a fish, animal, bovine or marine gelatin or vegetal gelatin-like product, a polysaccharide, a cellulosic material, pectin such as from fruits, or other suitable base. Other materials may be added to the base gel, for example to stabilize, add other effects flavor etc. The carrier or soluble base material may be inert, or may itself have an activity or other desired property, whether in relation to the primary purpose of the invention or otherwise.

Active agents may be used either impregnated in the strip material, added later, layered in a fashion so that an adhesive strip is separate from an active layer strip; the provision of strips that can encompass or otherwise carry one or more active ingredient strips, liquids, etc. in a pouch or encapsulation such that administration of various active ingredients can be achieved via attachment of an active ingredient container to the soft palate adhesive strip. Time release and slow release aspects of delivery can be achieved via suitable selection of permeable barriers employed to contain active ingredients and then the association of such barriers to soft palate adhesive strips. The layering of strip for separate and distinct purposes of structural tissue support versus for administering active ingredients is a entire segment of different embodiments of the present invention.

Components that can be included in strips or associated with strips in the various ways described herein include agents that may include additional active ingredients, including a plurality of active ingredients having an activity in relation to a particular condition or the throat or throat disorder, oral conditions, open skin or wound healing or repair agents and/or active ingredients having other desired activity.

Preferably in certain embodiments, active ingredients include at least one active ingredient with physical (moisturizing, lubricating, cooling etc) or pharmacological (for example decongestant, anti-histamine, anti-bacterial, anti-inflammatory, analgesic etc) activity. For example, active ingredients might include ingredients having any desired physical or pharmacological activity on the mucous membranes of the throat, including without limitation decongestants, lubricants, antibacterial and antiseptic compositions, anti-histamines, anti-inflammatory compositions, analgesics, and other medicaments and non-medicaments. Additional ingredients may include breath-fresheners and deodorizers. Inactive ingredients may be added in suspension or solution for example to stabilize or preserve the soluble base, balance the pH of the base, bring the base to closer approximation to isotonic concentration etc. The composition may additionally include adjuvants and the like such as vitamins for example selected from Ascorbic acid (vitamin C) which enhance the active ingredient effect. The composition may include additional ingredients for formulation purposes, for example selected from sodium chloride which maintains favorable isotonicity.

In still other embodiments, the use of additional ingredients may provide for chemical binding, and for example for the use of liposome technology, can be employed. In some embodiments of the invention a part or all of the active ingredients are encapsulated within encapsulation structures selected to provide the desired degree of adhesion to the mucous membranes of the throat, and adapted to release the active ingredients slowly over time in situ. These encapsulation structures may be distributed within the base material in the strip composition. In one embodiment, the encapsulation structures comprise multilamellar microparticles. The multilamellar microparticles are selected to exhibit good adhesion to the mucous membranes of the throat, and are small enough to be effectively distributed in the strip. The multiple layers may be structured to give slow release of the active ingredient over the desired time period, so that a single strip dose gives sustained activity over time, for example providing for measurable activity for a sustained period of four or more hours, and ideally of for example 6 to 12 hours, to give overnight effectiveness.

Microparticles are preferably sized and shaped to form an effective distribution within the base material in the strip as a composition in accordance with the invention. The microparticles in particular comprise generally spherical particles or microspheres. Particle sizes in the range 0.1 to 50 .mu.m, and for example 1 to 20 .mu.m are likely to be preferred. Particle levels of 5-25% within the composition are preferred but depend on the particular tissue characteristics being addressed.

Microparticles may be are adapted to facilitate slow release of the active ingredients over time, and are preferably inherently able to show good adhesion to the mucous membranes of the throat. Active ingredients are thus stabilized in situ on the mucous membranes at the back of the throat, and then released steadily at the site where they are required.

Using the present invention, it becomes possible to maintain reasonable levels of activity over the sort of time scale necessary to be effective overnight, and for example to assist in providing a relatively less disturbed night's sleep. Microparticles comprise multiple layered structures formulated with one or more of: surfactant layers (comprising any type of surfactant such as anionic, non-anionic, cationic, phospholipids and the like such as sucroesters and guar hydroxypropyltrimonium chloride), and hydrophobic or lipophilic materials such as aliphatic and aromatic hydrocarbons, optionally halogenated, higher alcohols, ketones and the like, for example including Vitamins (A, E, D), carotenoides, polyphenols, vegetable oils, essential oils, phytosterols, lipophilic preservatives, menthol, linalool, eucalyptol, and the like; and polar layers including solvents or polar media such as water, glycerol, PEG, sorbitol, glycol, hydrophilic materials such as alcohols or ethoxylated alcohols, carboxylic acids or salt of a fatty acid, quaternary ammonium derivatives, sulphonates or sulphates and the like, vitamins (B, C), flavonoides, 18-beta glycyrrhetinic acid and derivatives, glycerol, active ingredients such as plant extract as hereinbefore defined; hydrophilic preservative; cellulose polymer, hyaluronic acid and derivatives, alpha-hydroxide acid, and the like. Also possible inclusion are pectin; cellulose; sodium hyaluronate; guar hydroxypropyltrimonium chloride; polysorbate 60, and optionally additionally cellulose; xanthan gum; chitosan or quaternary ammonium. In one embodiment, such strip composition comprises: solvent 30-60%, Humectant 8-14%, Texturant 0-2%, Preservative 0-2%, and an Acidity regulator 0-1% (all by weight). Microparticles thus preferably comprise multilamellar structures of surfactant layers, which are able to encapsulate active ingredients to a very high degree for protection and controlled release—whether that be rapid release (e.g. for certain tissue stiffening components) or longer term release, such as breath freshing components). The strips are formulated to be adapted to enhance adhesion to human skin, and hence to fix the particles in position on the mucous membranes of the throat. Suitable compositions include 30 to 50% surfactant, 30 to 50% polar medium, and 10 to 60% active binding agent, comprising hydrophilic and hydrophobic agents as appropriate.

Microparticles are advantageous to fix the active ingredients adsorbed within each shaped layer in position on the mucous membranes of the user, protect the active ingredients and slowly release them in situ, and might also assist in providing a desired lubricating effect. Active or inactive ingredients might be provided either encapsulated within the microparticles or separately in suspension or solution within the base for various purposes.

Formulation of oral drug strips involves the application of both aesthetic and performance characteristics such as strip-forming polymers, plasticizers, active pharmaceutical ingredient, sweetening agents, saliva stimulating agent, flavoring agents, coloring agents, stabilizing and thickening agents. From the regulatory perspectives, all excipients used in the formulation of oral drug strips should be approved for use in oral pharmaceutical dosage forms. For example, films that incorporate a pharmaceutically active ingredient are disclosed in expired U.S. Pat. No. 4,136,145 to Fuchs, et al. These films may be formed into a sheet, dried and then cut into individual doses.

With respect to manufacturing of strips, one of skill in the art will appreciate the various methods and components involved to achieve desired qualitative and quantitative aspects. For example, if a dissolvable strip is intended to last over a several hour period, the changes in content of materials used in the manufacture, for example, of breath strips, can be adjusted to lengthen the time it takes to dissolve such strip. Flavor, binding and adhesion abilities, etc. are adjusted suitably to achieve desired results. Thus, while the present specification provides some detail as to how to make and use certain embodiments of the present invention, reliance on incorporation by reference is appropriate to encompass the myriad of ways in which a particular product is produced. All of such techniques, however, are well within the skill of one of ordinary skill in the art in view of the guidance and direction provided herein.

Preferably the strips of the present invention are made in a manner that do not dissolve in fewer than ten seconds, thus distinguishing the same from common breath strips widely available. The strips of the present invention may have a weight of from 30 to several hundred mg., preferably over 33 mg. Preferably, strips of the present invention have sufficiently high moisture content to impart the product with flexibility and to avoid becoming brittle, e.g. the strips should preferably avoid cracking when bent.

In certain embodiments, the methods employed by MonoSol Rx with respect to a thin film drug delivery technology can be used, preferably providing a strip having a relatively thin film, which is similar in size, shape and thickness to a postage stamp. Preferably, the strips of the present invention, when containing active ingredients, have the ability to carry doses of prescription products up to 80 mg or exceeding 1000 mg, and even more preferably, over 200 mg. Suitable taste masking agents can be employed depending upon the active ingredients involved.

Other embodiments of the present invention are directed to multiple film laminates that can have distinct adherence and qualitative features and components associated with separate layers, thus facilitating differences in manufacture, activity, structural characteristics, such as flexibility, dissolution rate, etc. The strips of the present invention provide the requisite pliability and tensile strength necessary to securely adhere to a person's mucosal tissues for at least one hour, more preferably at least two hours, and even preferably a bioadhesive polymer is selected from the group consisting of polycarbophil, carbomer, one or more acrylic polymers, one or more polyacrylic acids, copolymers of these polymers, a water soluble salt of a co-polymer of methyl vinyl ether and maleic acid or anhydride, a combination thereof and their salts.

In other embodiments, to achieve the desired thickness of strips for structural support purposes of the present invention, a so-called slab or sheet manufacturing technique is employed that uses a nonaqueous, extrudable composition comprising at least one thermoplastic polymer in an amount of more than 20 wt % of the whole composition, such composition comprising at least one thermoplastic polymer and one or more bioactive ingredients in a form that may be placed on the mucosa and having an average dissolution time of preferably more than 50 minutes, more preferably at least about 2 hours, and even more preferably at least about 5 hours. In some embodiments the strip is in a sheet and has a surface area of approximately 0.25-1.5 in. and a thickness of approximately 10-70 mil. A strip may be impregnated or coated with a dose of active ingredient and other components. Preferably, strips of the present invention comprise a mixture of at least three types of film forming agents, such as maltodextrins, fillers (for example, microcrystalline cellulose (MCC)) and hydrocolloids (for example, sodium aliginate), suitably adapted to adhere to oral surfaces of an oral cavity, and in particular the soft palate. While structural support for the soft palate is the principal direction of the present invention, embodiments also comprise the use of such strips to deliver or release oral care agent(s). Such agents include anti-microbial agents and salivary stimulants to treat, for example, halitosis, dental plaque, gingivitis, xerostomia, dry mouth, like oral conditions or combinations thereof. Further, the oral care edible film can act as a breath freshener effective against malodor. In other embodiments, both a longer acting (if not entirely non-dissolvable strip) can be employed in association with one or more other strips having other desired characteristics. For example, a structural support strip can be used to achieve breath freshening, delivery of a medicinal compound, etc.—with such second strip having entirely distinct dissolution characteristics.

The oral cleansing and breath freshening effects of the edible film of the present invention can be achieved by entrapping the oral care agents within the oral cavity to provide extended efficacy. In this regard, the highly dissolvable edible film can act as a medium through which a pharmaceutically active oral agent can be administered via a mucous membrane of the oral cavity.

Strips may further include a variety of other suitable ingredients, such as softeners, colorants, flavoring agents, emulsifiers, surface active agents, thickening agents, binding agents, sweeteners, fragrances, other like ingredients or combinations thereof.

The strips may comprise a hydrocolloid of any suitable type, amount and number of hydrocolloids. In an embodiment, the hydrocolloid can constitute between about 10% to about 50% by dry weight of the edible film, preferably about 20% to about 30% by dry weight. The hydrocolloid can be derived from, for example, natural seaweeds, natural seed gum, natural plant exudates, natural fiber extracts, biosynthetic gums, gelatins, biosynthetic process starch or cellulosic materials, alginates, sodium alginate, calcium alginate, carrageenans, guar gum, locust gum, tara gum, gum arabic, ghatti gum, agar gum, xanthan gum, pectin, other like hydrocolloid source material or combinations thereof.

In certain embodiments of the present invention, the size and number of adhesive strips contacting the soft palate of a person can be varied. For example, while a larger size strip (e.g. an expanse of material that covers a particular area of soft palate tissue) can be greater than the dimensional area of a person's soft palate, thereby extending beyond the perimeter of the soft palate, it can also be of a smaller area and may extend therefore over only some, e.g. a central portion; half of the area of the soft palate—leaving the other side of the soft palate area uncovered by any strip, etc. Moreover, more than one strip can be employed to attach to the soft palate region, such as by providing two separate smaller strips on the soft palate with some space between, more preferably at least three or more individual strips within the soft palate region.

Incorporated herein by this reference is 2011/0009834 to Asmussen with respect to various particular components that can be utilized to form strips. The strip-shaped forms can comprise a flexible material suitable for pharmaceutical and/or cosmetic use by humans and/or in animals, i.e. materials that do not have any unwanted side effects. Unwanted side effects would be toxic effects, the causing of irritations or the triggering of allergic reactions, for example. Suitable materials may be, for example, thermoplastic polymers, thermoset polymers, copolymer films, paper, waxes, textiles (nonwovens, knitted fabrics and woven fabrics), chalks, films, gels and wood composites, as well as combinations of the aforementioned materials. Specific polymers suitable as material for the strips may be selected from the group of polymers consisting of cellulose ethers, methyl acrylates, hydroxyalkyl celluloses such as hydroxypropyl methyl cellulose, hydroxypropyl cellulose, hydroxyethyl cellulose, methyl cellulose and carboxymethyl cellulose, polysulfones, polyvinyl pyrrolidones, crosslinked polyvinyl pyrrolidones, polyvinyl pyrrolidone-vinyl acetate copolymers, polyvinyl alcohols, polyacrylic acids, polyacrylate polymers, crosslinked polyacrylic acids, polyethylene oxides, polyethylene glycols, polyvinyl alkyl ether-maleic acid imide copolymers and carboxyvinyl polymers. Suitable polymers may also be selected from the group of polymers consisting of marine colloids, natural gums and polysaccharides. These polymers include, for example, sodium alginate, carrageenan, xanthan gum, gum acacia, gum arabic, guar gum, pullulan, agar, chitin, chitosan, pectin, karaya gum, zein, hordein, gliadin, carob meal, tragacanth and other polysaccharides, starches such as maltodextrins, amylose, amylopectin, maize starch, potato starch, rice starch, tapioca starch, pea starch, sweet potato starch, barley starch, wheat starch, waxy maize starch, modified starch, dextrins, levan, elsinan and gluten; and proteins such as collagen, whey protein, casein, milk protein, soya protein, gelatine, waxes and colophony, as well as synthetic waxes and bees wax. By combining two or more of the aforementioned polymers, the properties of the strip of material, such as mucoadhesiveness, flexibility, solubility behaviour, swelling behaviour and the like, can be adapted according to one's wishes and requirements. The strip of material, or the layers of the strip of material, comprise/comprises at least one polymer, which represents an essential component of the strip of material or of the layer(s). The polymer portion amounts to at least 5%-wt. and preferably not more than 90%-wt., preferably 10 to 70%-wt., more preferably 30 to 60%-wt., in each case relative to the strip of material or the layer, respectively. The strip of material, or individual layers of the strip of material, can furthermore contain excipients or additives in order to control the chemical or physical properties, such as flexibility, mucoadhesive properties, disintegratability, swellability and/or diffusion properties. To be taken into consideration as excipients or additives are, in particular, substances selected from the group consisting of antioxidants, emulsifiers, gelling agents, flavour enhancers, taste corrigents, flavours, sweeteners, stabilisers, pH regulators, acidifying agents, bulking agents, preservatives, colourings, thickening agents, plasticisers and humectants. Those skilled in the art will know suitable excipients and additives approved for pharmaceutical applications.

In one embodiment, the strip has a surface adapted to promote tissue in-growth, and in other embodiments, the growth of desired bacteria, especially those bacteria modified as described herein, such as via a CRISPR-Cas system. The in-growth promoting surface is desirably selected from a group of outer surfaces including a textured surface, a porous surface, a braided surface, a mesh surface, a fleece surface, and a coating for inducing bone or tissue in-growth.

Various embodiments are directed to a buccal bioadhesive strip, that when applied to the soft palate, has a surface that is anti-microbial in nature, preferably one that *S. pyogenes* cannot readily adhere to, such that such strips assist in reducing the surface area in the mouth where *S. pyogenes* can exist and grow. Such strips also have the attribute of preventing noxious odors that may arise due to the proliferation of foul smelling agents produced by bacteria that can survive in one's mouth.

Other embodiments are directed to a buccal bioadhesive strip adapted to be attached to the tissue of the soft palate, such strip including at least one surface that has a pattern defined by a plurality of spaced apart features each having at least one microscale dimension and having at least one neighboring feature having a substantially different geometry, wherein an average spacing between adjacent ones of said features is between 0.5 and 5 .mu.m.

Preferably, the strip has a first and second side, the first side having a bioadhesive that is adapted to bind to a mucosal membrane for at least 1 hour while inside a person's mouth, wherein the strip extends over a majority of the soft palate. In certain embodiments, the strip includes xylitol and at least one encapsulated pocket containing one of an analgesic, a solution containing a LAB, selected from the group consisting of a LAB that coaggregate with *S. pyogenes*. Preferably the strip reduces the adhesion of *S. pyogenes* to the epithelial tissue of a person's mouth and also includes between 0.2 and 0.9% xylitol by weight. Certain strips are made with bioluminescent material and/or material that reacts specifically with ultraviolet light to kill bacteria on the strip. Projection of UV light onto the strip to destroy bacteria after a certain amount of time is one aspect of the present invention. While the strip may be non-dissolvable in a person's mouth, preferably it is dissolvable in a person's mouth within a period of 3 hours.

In certain embodiments, a mucosal adhesive strip has a coated surface for resisting bioadhesion that includes at least one patterned polymer including coating layer having a plurality of features attached to or projected into a base surface. The features each have at least one microscale (<1 mm) dimension and have at least one neighboring feature having a substantially different geometry. The patterned coating layer preferably provides an average roughness factor (R) of from 4 to 50. The coating layer resists or enhances bioadhesion as compared to the base surface. An article having a surface coating with topography for controlling bioadhesion comprises a base surface, at least one patterned polymer comprising coating layer including a plurality of spaced apart features attached to or projected into the base surface which provide at least a first feature spacing distance. The features each have at least one microscale dimension and at least one neighboring feature having a substantially different geometry. The coating layer provides an average roughness factor (R) of from 2 to 50, preferably being from 4 to 50. The coating layer resists or enhances bioadhesion as compared to the base surface.

Still other embodiments include the use of bacteria that have been modified to remove or disable one or more virulence factors of the particular bacteria. Key virulence factors present in GAS include streptococcal pyrogenic exotoxin (SPE)-B, the hyaluronan synthesis operon and active superantigen against human immune cells. A key event in the ability of GAS to cause severe invasive streptococcal infection is the acquisition of novel genetic traits. During severe invasive infection, however, GAS destroys its own covRS (for "control of virulence genes") two-component system, which negatively regulates many virulence factor genes, resulting in a hyper-virulent phenotype. Modification of GAS, preferably using CRISPR-Cas and Cpl1, can address such virulent strains and thus control the infections.

These modified bacteria, especially those that demonstrate human specificity, are used to competitively inhibit or to otherwise populate tissue surfaces, such as the oral cavity, to prevent a variety of diseases. In this regard, one aspect of the present invention is directed to the modification of certain human-specific pathogens by targeting one or more virulence factors thereof, preferably by using CRISPR-Cas or CRISPR-Cpl1 systems, to excise virulence factors genes, or at least portions thereof or transcriptional or translational controls therefore, such that such pathogenic pathogens are deprived of their undesired pathogenic characteristics. One of skill in the art can readily assess the number and identity of human-specific pathogens, as well as the particular virulence factors associated therewith, and can then, employing the CRISPR systems as referenced herein, remove, render incapable or otherwise disable the virulence facts of such microorganisms such that they no long pose a pathogenic threat to humans. In various aspects of the present invention, there is a purposeful exposure of individuals to such modified pathogens such that the population of the same, for example in the oral cavity or the human gut, competitively inhibits the infection of non-modified pathogenic microbes of the same species. In one particular embodiment, S. pyogenes is modified to render ineffective one or more virulence facts such that the progression of a sore throat is avoided.

The concerns relating to possible unintended consequences from the genetic modification of genomes, especially the human genome, are largely if not entirely addressed in various embodiments of the present invention as modifications are not being made to the human genome—but rather to microbes. Moreover, in preferred embodiments, the microbes modified are limited to those demonstrating human tropism such that undesired and unintended changes to other animals and organisms are not affected and that the only implications of such genomic alterations of human specific pathogens are restricted to such species in a manner that is not capable of affecting other than the particular human disease at issue. This can include, for example, modifications and/or employment of integrons, which are a two-component genetic recombination system present in the chromosome of many bacterial species. The integron incorporates mobile genes termed gene cassettes into a reserved genetic site via site-specific recombination, named the Integron/gene cassette system. The integron consists of three basic elements: an integrase gene, an attachment site and a promoter. These elements can be manipulated to, for example, decrease the ability of a dominant S. pyogenes population in one's mouth from being able to effectively attach to epithelial tissue; or alternatively, to coaggregate with other bacteria so as to be swalled and removed from the oral cavity, etc.

BRIEF DESCRIPTION OF THE FIGURES

FIG. 10 is an illustration of a pre-made sheet of sore throat strips that can be disassociated with the sheet and then applied to mucosal membranes.

FIG. 11 is a side view of one embodiment of a sore throat strip having an outer layer, an adhesive layer, a layer with an encapsulated agent contained there between.

FIG. 12 is a side view of one embodiment where the encapsulated agent is encapsulated into small beads that are frangible via pressure of an individual's tongue pressing against the strip so as to force it into the roof of a person's mouth.

DETAILED DESCRIPTION OF CERTAIN PREFERRED EMBODIMENTS

In various embodiments, the present invention includes a soluble composition for the administration of an active ingredient to a site on the mucus membranes of the throat of a human. A sore throat is initially mostly viral in nature and common viruses may provide an initial conditioning to the host mucosa that favors bacterial adherence which subsequently leads to bacterial biofilm formation. To overcome the adhesion of the pathogens to the host mucosa is a viable strategy in preventing infection. Additionally, the use of effective inhibitory agents may also exert a therapeutic advantage by inhibiting extended colonization and restricting the spread of infection. Employment of the strips as described herein can alleviate the onset and the progression of sore throat via the various structures and functions as set forth herein.

The sore throat strips 10 are applied in a temporary rather than permanent manner. No prior art method or device employed in the battle against sore throats offers such a variety and flexibility of treatment options as do the various embodiments of the present invention.

Figure 1:
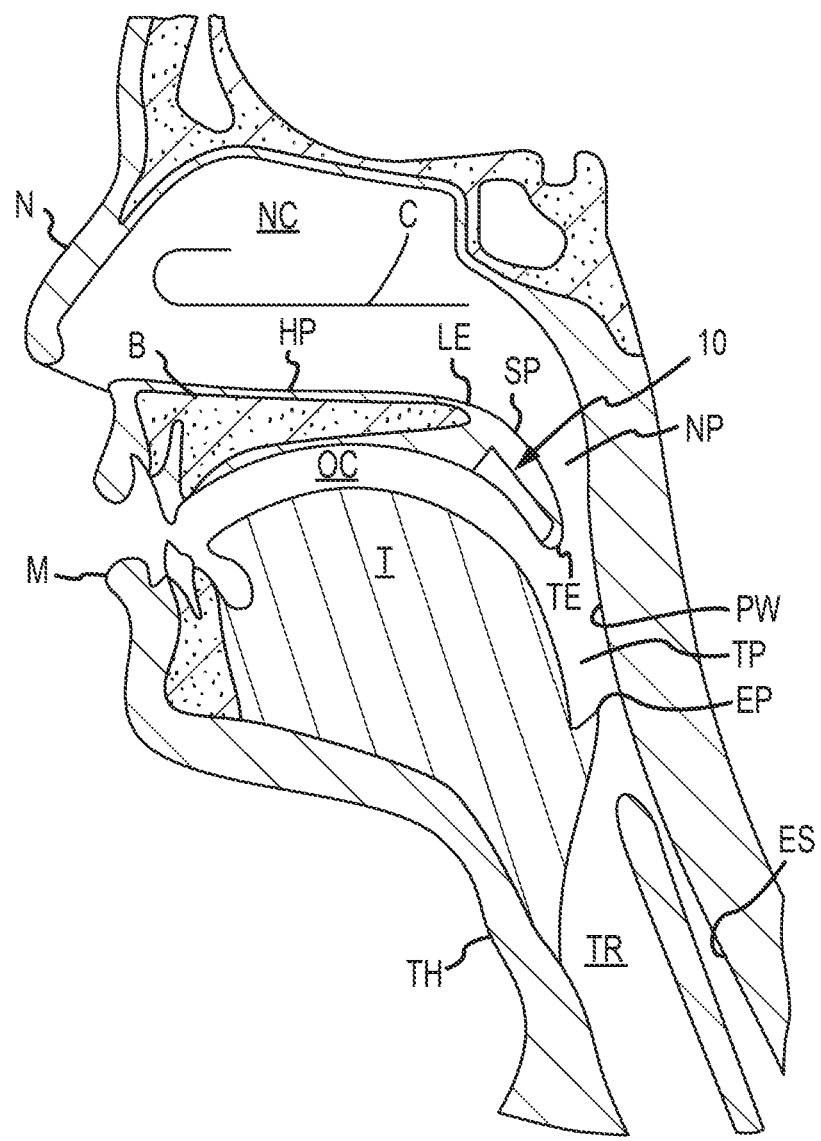
FIG. 1 is a cross-sectional view of a person's airway where a particular placement of a strip is shown associated with the soft palate.

FIG. 1 shows, in cross-section, a naso-pharyngeal area of an untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area of the patient with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces mean surfaces exposed to air. Both the upper and lower surfaces of the soft palate SP are outer surfaces.

Figure 2A:
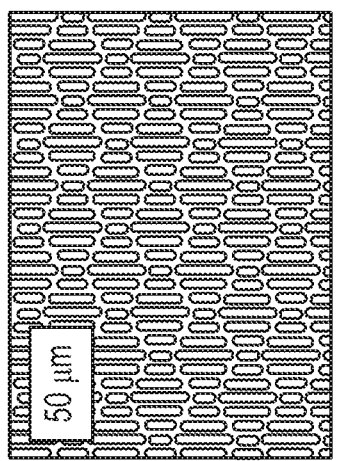
FIG. 2(a)-(d) illustrate some exemplary surface architectural patterns according to the invention.
Figure 2B:
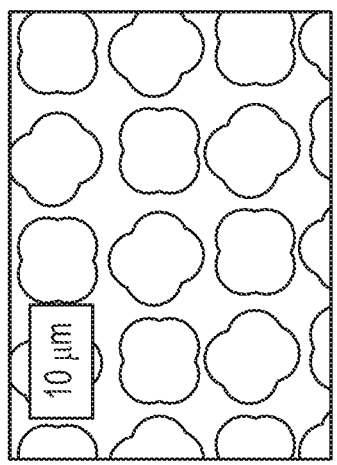
Figure 2C:
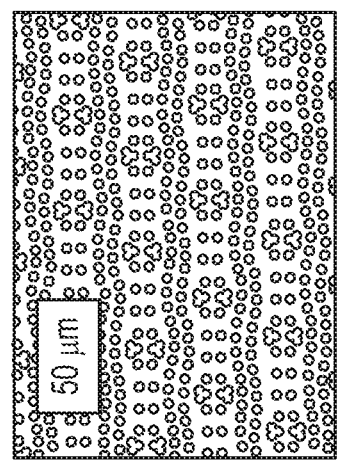
Figure 2D:
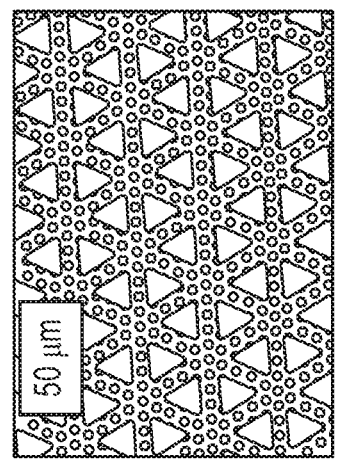

FIGS. 2(a)-(d) illustrate some exemplary architectural patterns that can be used with the invention. FIG. 2(a) shows a riblet pattern having features spaced about 2 μm apart; FIG. 2(b) shows a star/clover pattern, FIG. 2(c) a gradient pattern, while FIG. 2(d) shows a triangle/circle pattern.

Figure 3:
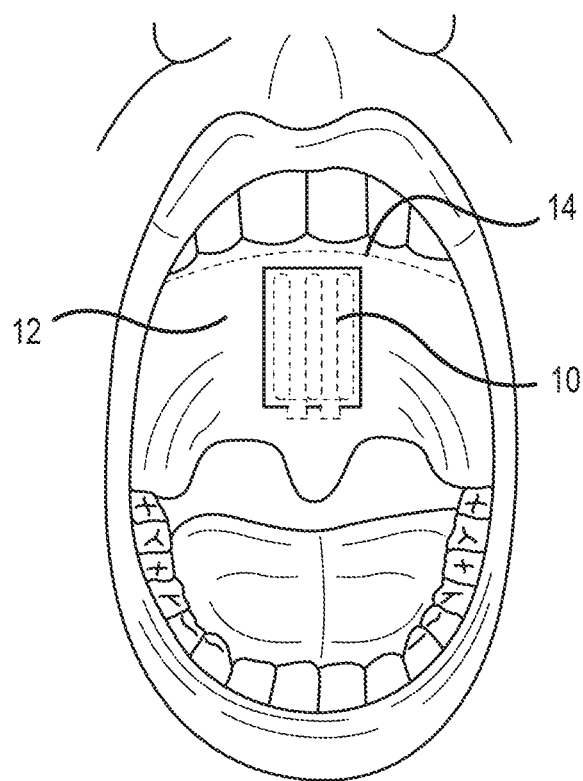
FIG. 3 is a front perspective view of a person's open mouth, illustrating the placement of a strip on the surface of the soft palate.

FIG. 3 is a front perspective view of a person's open mouth, illustrating the placement of a sore throat strip 10 on the surface of the soft palate 12 and the hard palate/soft palate junction 14. The area of tissue to be covered can be addressed by either having the person provide strips 10 side-by-side to cover the area; by having certain tissue areas provided with thicker ultimate strip depth than other areas (e.g. providing for the option of stiffening certain palate soft tissue 12 more than directly adjacent tissue), and even providing strips 10 having different characteristics in terms of a variety of factors, such as taste, composition, adherence or dissolvability characteristics, area, shape, thickness, flavor, duration of flexibility characteristics, etc. Films may be selected of desired thickness and having desired properties in terms of dissolving rate, flexibility, provision of stiffness over time, adhesion duration, ability to cause reversible contraction of soft palate 12 tissue and can be fashioned, by cutting, forming in a particular mold, etc. to cover a desired soft palate 12 area. Custom strips 10 or films having particular shapes, such as one that covers the particular area of that particular person's soft palate 12 tissue region, is contemplated.

Figure 4A:
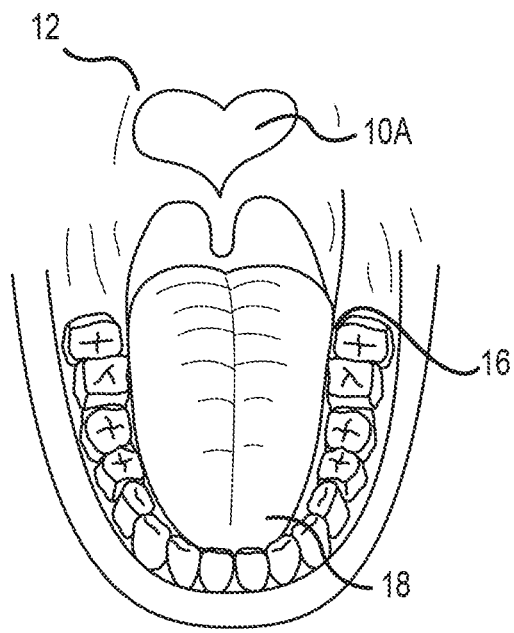
FIG. 4A is an illustration of a person's mouth with a heart-shaped strip associated with the soft palate.

FIG. 4A is an illustration of a person's mouth and tongue 18 with a heart-shaped sore throat strip 10A associated with the soft palate 12 and a teeth anchor 16 associated with such sore throat strip 10A.

Figure 4B:
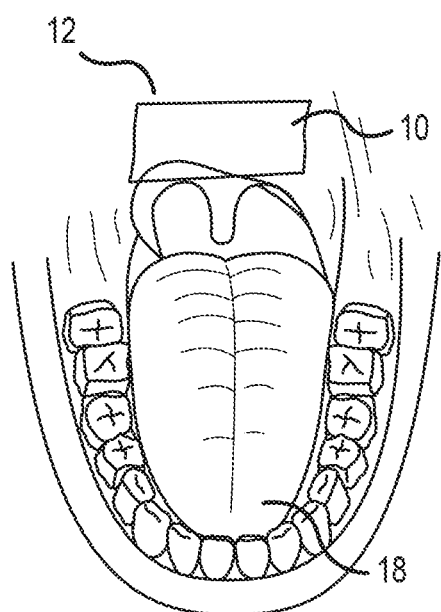
FIG. 4B is an illustration of a person's mouth with a rectangular shaped strip adhered to the soft palate with mucosal adhesive agents.

FIG. 4B is an illustration of a person's mouth and tongue 18 with a rectangular shaped sore throat strip 10 adhered to the soft palate 12 with mucosal adhesive agents. The strip 10 may be of any suitable shape, for example being square or rectangular for ease of storage, placement, distribution in packages, but is preferably generally planar and approximately 0.5 to 2 cm in length and breadth. Again, the particular shape and dimensions of a strip 10 can be varied as required to address individual issues, the degree of tissue stiffness of the soft palate 12 required to address a particular issue, etc. Thus, one aspect of the present invention is that a person may modify the number, placement, kind, type, shape, time of application, frequency of application, etc. to address particular situations, which may vary over time and under any given set of circumstances. The customization of such a strip 10 in terms of shape, size, characteristics regarding flavor, thickness, adhesive qualities etc. are within the present scope of the invention.

Figure 5:
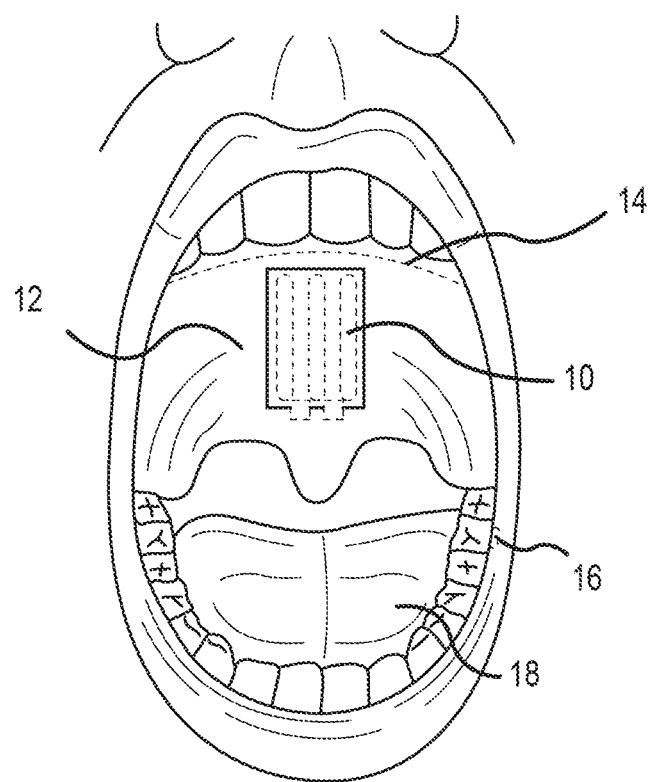
FIG. 5 is an illustration of a person's open mouth with a strip place on the soft palate.

FIG. 5 is an illustration of a person's open mouth and tongue with a sore throat strip 10 placed on the soft palate 12 and a dental floss attachment anchor 16 associated between the strip 10 and a the teeth. To avoid fears that adhesion will not suffice to attach a strip 10 to a person's soft palate 12 tissue, strips 10 can also be afforded an attachment line, such as dental floss, so that the strip can be also anchored to one's teeth, tooth or around the tongue 18 to ensure that the strip 10 does not present a choking hazard if detached. Thus, in one embodiment, a loop or segment of dental floss anchored to teeth or around gum line or a tongue 18 can prevent swallowing of the strip 10 if it becomes detached. FIG. 5 further shows the hard palate/soft palate junction 14.

Figure 6A:
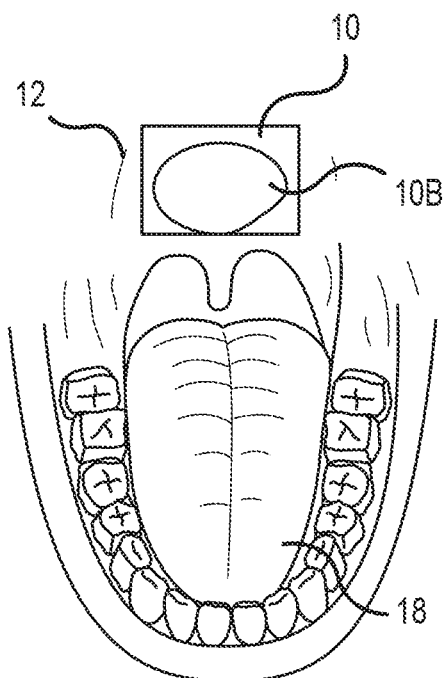
FIG. 6A is an illustration of a person's open mouth where a first rectangular strip is over-laid by a 2nd circular strip.

FIG. 6A is an illustration of a person's open mouth and tongue 18 where a first rectangular sore throat strip 10 is over-laid by a 2nd circular sore throat strip 10B. In one embodiment, the strips 10 employed provide more structural integrity to soft palate 12 tissues upon which such strips 10 adhere, and also have long term function (from at least about 5 minutes to several hours), preferably for at least about 3 hours, more preferably at least about 5 hours and most preferably at least about 6 or more hours—roughly equating to the period of time of a person's sleep. The mucosal strips 10 are designed to adhere well with each other when placed on palate tissue 12 so that layering of the strips 10 can be accomplished so as to custom build a desired thickness of the strips 10 over tissue to be covered. This permits a user to layer as many strips 10 as deemed necessary to stiffen the soft palate 12 tissue in a manner that is personally comfortable for such user while also being sufficient to address the particular issue experienced by such user.

Figure 6B:
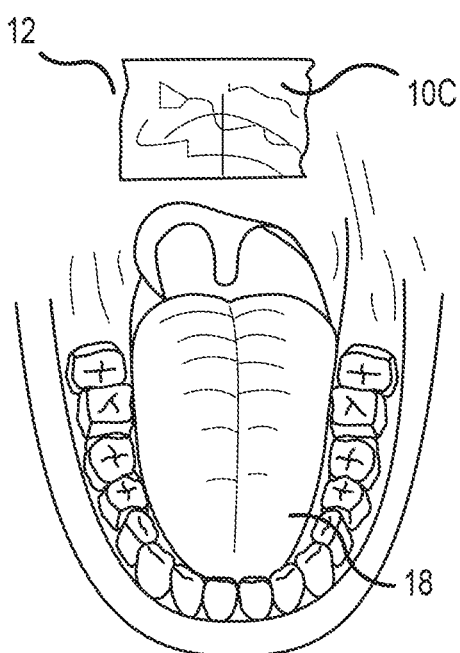
FIG. 6B illustrates a strip having structural support elements associated therewith.

FIG. 6B illustrates a sore throat strip 10 positioned above a person's tongue 18 having structural support elements 10C associated therewith. The sore throat strip 10 of the present invention may further include one or more compositions, or alternatively, may solely be provided with materials meant and intended solely to provide desired structural support to reduce vibrational movement of soft palate 12 tissues. Active agents may be used either impregnated in the strip 10 material, added later (e.g. agents can be sprayed on such strips 10), layered in a fashion so that an adhesive strip 10 is separate from an active layer strip 10; the provision of strips 10 that can encompass or otherwise carry one or more active ingredient strips 10, liquids, etc. in a pouch (not shown) such that administration of various active ingredients can be achieved via attachment of an active ingredient container to the soft palate 12 adhesive strip 10. Time release and slow release aspects of delivery can be achieved via suitable selection of permeable barriers employed to contain active ingredients and then the association of such barriers to soft palate 12 adhesive strips 10.

Figure 7:
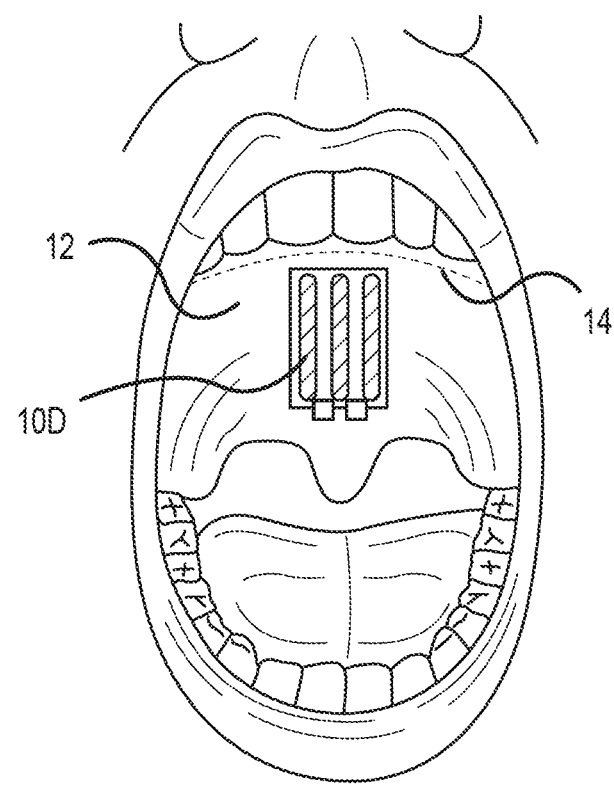
FIG. 7 illustrates a sore throat strip having cross-hatched support structure integral with the strip, said cross-hatched support structure also including encapsulated agents, such as an antibiotic; lactic acid bacteria; S. pyogenes modified by a CRISPR-Cas system to reduce one or more virulence factors; and a breath mint solution.

FIG. 7 illustrates a sore throat strip 10 having a cross-hatched support structure 10D integral with the strip 10 to provide desired damping of vibrational movement of the soft palate 12. In one embodiment, the strips 10 can comprise collagen or other tissue growth enhancing material to further the stiffening of the soft palate 12 so as to reduce the occurrence of vibration when a person is sleeping. In still other embodiments, the strips 10 are positioned to overlap with the hard palate junction 14 as well as the soft palate 12.

Figure 8:
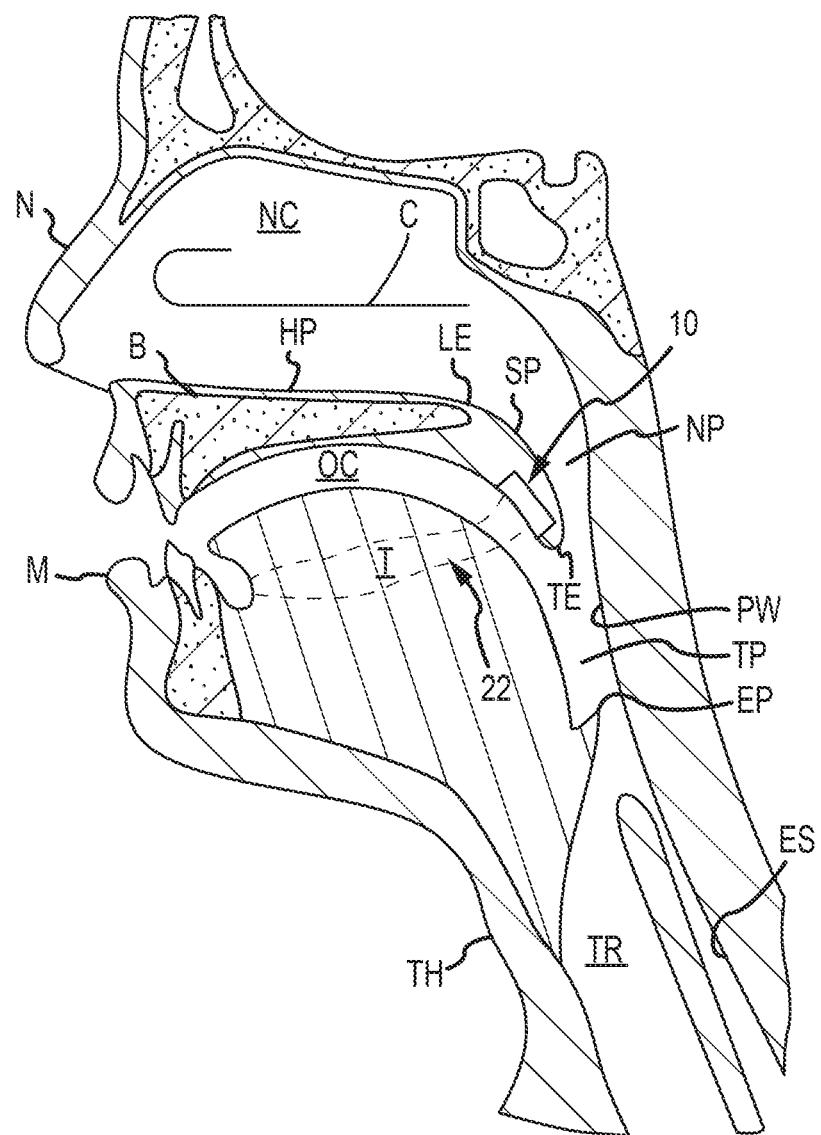
FIG. 8 is a cross-sectional view of a person's head where a sore throat strip is anchored by a tongue loop anchor.

FIG. 8 is a cross-sectional view of a person's head where a sore throat strip 10 is anchored by a tongue loop anchor 22. The general objective of placing one or more strips 10 in or about the soft palate 12 region is intended to provide required structural support for the tissue in a manner that reduces the instances of vibration of such tissues. So in certain embodiments, strips 10 of various desired shapes and sizes can be employed to populate the area of one's soft palate 12 to dampen vibrational movement caused by the passage of air through the region when asleep. In some individuals, the surface area of adhesive strips 10 will be relatively minor as compared to others, who may require substantially all of the soft palate 12 tissue area to be covered to achieve relief from sore throat.

Figure 9:
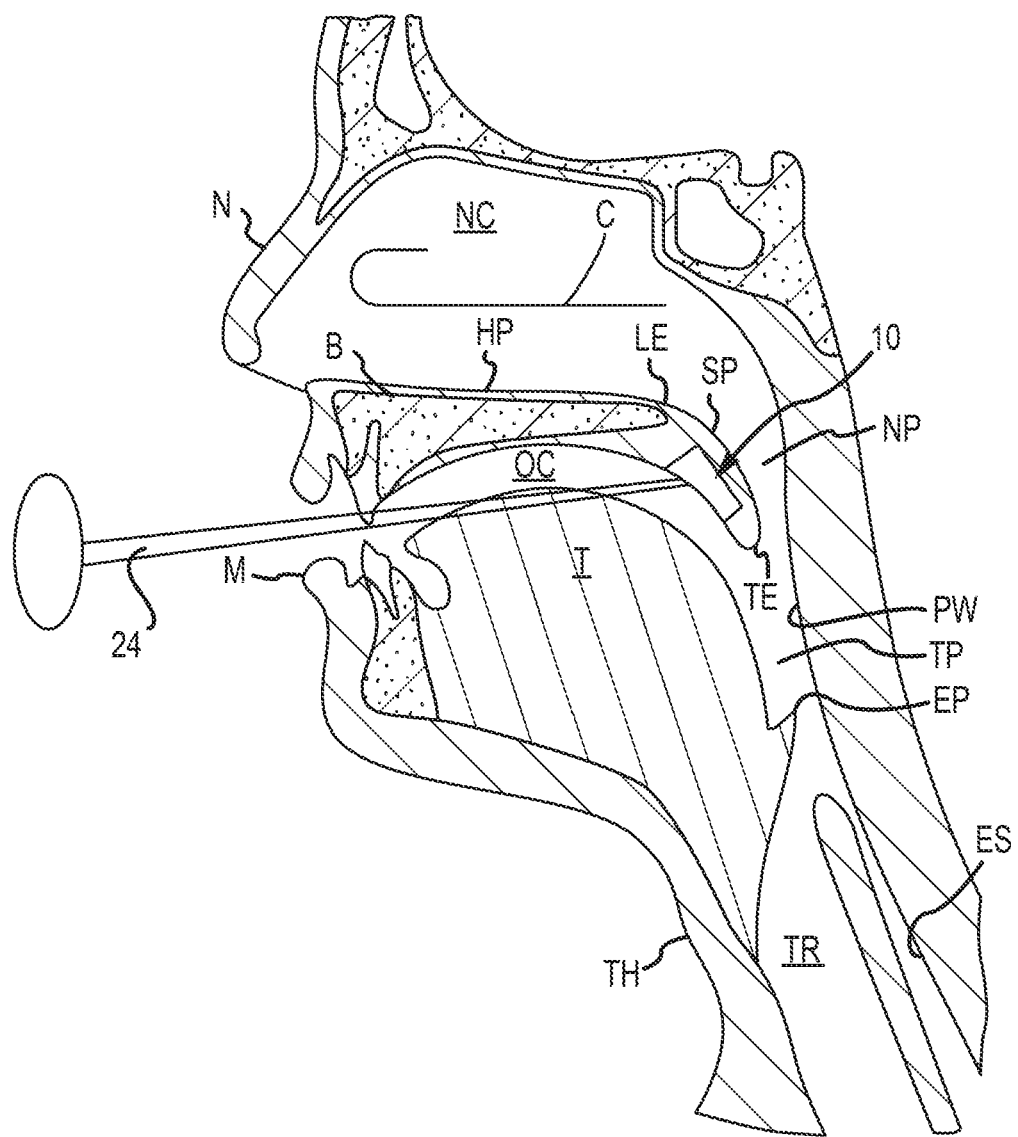
FIG. 9 illustrates a strip applicator for placing a sore throat strip properly on the roof of an individual's mouth.

FIG. 9 illustrates a strip applicator 24 for placing a sore throat strip 10 properly on the soft palate 12. Preferably the strip 10 (or strips, whether layered, certain portions more dissolvable than others, etc.) are positioned on a person's soft palate 12. This can be achieved via a person's fingers or through the use of an applicator 24 (otherwise described and illustrated.) The strip 10 is particularly suited to delivery of ingredients having activity in relation to the mucosa of the throat, in particular at the soft tissue 12 in the pharyngeal region of the back of the throat, to keep the pharyngeal membranes moist and lubricated. The strip 10 is conformed as a relatively thin planar structure to facilitate desired rates of inter-oral dissolution. For example, in certain embodiments, a single strip 10 may be preferably no more than about 150 micron thick, more preferably in the range 100-400 micron thick, and in other embodiments may be over 500 microns in thickness. In other embodiments, however, the ability to layer strips 10 on top of one another provides for the manufacture and availability of strips 10 of more traditional thickness, such as those for example of the breath strips of Listerine, etc.

Reference herein to a strip 10 is to any soluble prolonged release presentation of the composition which is conformable and is adapted to lie in a subject's mouth without causing obstruction or interfering with breathing, talking or swallowing or the like, or to conform to the surface of a subjects open skin or wound. Preferably the strip 10 comprises a flexible film or the like. In use, the strip 10 to be placed in a subject's mouth is intended to be placed at the back of the throat.

Components that can be included in strips 10 or associated with strips 10 in the various ways described herein include agents that may include additional active ingredients, including a plurality of active ingredients having an activity in relation to a particular condition or the throat or throat disorder, oral conditions, or open skin or wound healing or repair agents and/or active ingredients having other desired activity.

In still other embodiments, the use of additional ingredients may provide for chemical binding, and for example for the use of liposome technology, can be employed. In some embodiments of the invention a part or all of the active ingredients are encapsulated within encapsulation structures selected to provide the desired degree of adhesion to the mucous membranes of the throat, and adapted to release the active ingredients slowly over time in situ. These encapsulation structures may be distributed within the base material in the strip 10 composition. In one embodiment, the encapsulation structures comprise multilamellar microparticles.

The strips 10 preferably have a surface that is antimicrobial in nature, such that such strips 10 assist in reducing the surface area in the mouth where noxious odors may arise due to the proliferation of foul smelling agents produced by bacteria that can survive in one's mouth. With possible breath freshening components added to the strip 10, morning breath and bad breath issues would be addressed. One aspect of the present invention is directed to the novel combination of a specifically surface structured bioadhesively attachable, and in a preferred embodiment, dissolvable, strip 10 of material that persists in the mouth for at least one hour and preferably at least about 3 hours, so as to stiffen the tissue of the throat, specifically the soft palate 12. The ability to defeat the proliferation of bacteria in a person's mouth can significantly decrease the occurrence of so-called "morning breath".

Other embodiments employ differences in visual appearance to determine whether a strip 10 patch is placed properly; whether certain desired or undesired bacteria are present in the mouth, etc, and such effective means for determining the same include a film, coating or patch that includes one or more of the following characteristics: reflectance, retroreflectance, fluorescence, photoluminescent light transmission, color, tinting strength, and whiteness. In certain embodiments, the method may also assist in the detection of whether a person has a certain medical condition, such as strep throat. Thus, in one embodiment, the strip 10 patch changes color, expresses bioluminescence, etc. if there is strep bacteria present in a predetermined amount.

Preferably, a hydrophilic pressure-adhesive hydrogel is employed that has desirable characteristics. In one embodiment, a hydrophobic pressure-sensitive adhesive or bioadhesives is used to provide desired control of tack, adhesive and water sorption properties required for optimal application mucosal tissue. U.S. Pat. No. 5,166,233 to Kuroya, et al. is incorporated herein by this reference for suitable adhesives in this regard. U.S. Pat. No. 6,552,024 to Choi is likewise incorporated herein in its entirety by this reference, as is U.S. Pat. No. 7,906,140 to Bromley, et al.; U.S. Pat. No. 6,803,420 to Cleary et al.; U.S. Pat. No. 7,984,714 to Hausmann et al.; U.S. Pat. No. 7,276,246 to Zhang; U.S. Pat. No. 5,578,315 to Chien et al.; U.S. Pat. No. 7,470,397 to Meathrel et al. U.S. Pat. Publication No. 2011/0033542 to Myers, et al.; U.S. Pat. No. 7,138,135 to Chen; U.S. Pat. No. 7,441,559 to Nelson.

Thickness of strips can relate to dissolution time especially if certain formulae are used. Incorpoarated herein by this reference are the following with respect to strip production: wet cast monolayer film compositions for pharmaceutical and vitamin delivery are disclosed in Fuchs et al. U.S. Pat. No. 4,136,162; Schmidt discloses bilayer film compositions for pharmaceutical and food uses in U.S. Pat. No. 4,849,246, and Leung U.S. Pat. No. 6,923,981, Fuisz et al. US 20080075825, 20090098192 to Fuisz, Slominski et al US 20060207721, Fankhauser et al, US 2007/0202057, Laskey U.S. Pat. No. 1,492,600, Repka et al U.S. Pat. No. 6,375,963, Schiraldi; 20140065218 to Lang, et. al., U.S. Pat. No. 6,072,100, Yang et al. U.S. Pat. Nos. 7,357,891 and 7,425,292, and Pharmaceutical Extrusion Technology, edited by Issac Ghebre-Sellassie and Charles Martin (2007) also incorporated in their entireties by this reference. Also, for purposes of written description and enablement of the various embodiments of the present invention, the following published applications and issued patents are incorporated herein by this reference in their entireties: U.S. Pat. Nos. 7,067,116 and 7,648,712 to Bess, et al.; U.S. Pat. No. 7,632,525 to Dodds, et al.; U.S. Pat. No. 6,502,574 to Stevens, et al.; 20050159637 to Nelson et al.; U.S. Pat. No. 7,845,356 to Paraschac et al.; U.S. Pat. No. 7,824,588 to Yang et al.; 20090098192 to Fuisz; U.S. Pat. No. 7,500,484 to Nelson; Fentanyl compound-containing edible patch to be applied to oral mucosa, to Furusawa et al.; U.S. Pat. No. 7,566,310 to Badr et al.; U.S. Pat. No. 5,190,053 to Meer et al.; Schmidt U.S. Pat. Nos. 6,748,951 and 6,467,485; 20110009834 to Asmussen; U.S. Pat. No. 4,136,145 to Fuchs, et al. Various bioadhesive compositions comprising poly(acrylic acid) are described, e.g., in WO 98/22097; EP 410,696; U.S. Pat. Nos. 5,643,603; 4,915,948; 5,895,804 and 6,284,235, 7,143,709; 7,666,502; and U.S. Pat. Nos. 7,579,078. 7,650,848; U.S. Pat. Pub. No. 20060188813 to Shimada all of which are incorporated herein by this reference.

In one embodiment, the strips can comprise collagen or other tissue growth enhancing material to further the stiffening of the soft palate so as to reduce the occurrence of vibration when a person is sleeping. Collagen allows for the tissue in growth (tissue engineering). The collagen can be in many types and forms, or in combinations thereof. For example, collagen can be Type I, II or III. Collagen can be native, denatured or cross linked. The various types and forms of collagen are described generally in Methods in Enzymol. (1982) 82:3-217, Pt. A, the contents of which is incorporated by this reference. For example, collagen can be produced from animal derived tissues such as bovine hides, human tissues such as cadaver skin or human cell cultures or through recombinant methods.

For sore throat applications, the strip as described may also be loaded with analgesics and pain relievers in addition to the other active components described herein, thus providing a person with the ability to fight the infection and inflammation of tissue in the back of their throats while also achieving pain relief while doing so. In certain preferred embodiments of the present invention, the wood sugar xylitol is provided in the strip that attaches or adheres to the back of a person's throat.

*Streptococcus pyogenes* is a frequent colonizer of the respiratory tract mucosal surface, causes a variety of human diseases. *Lactobacilli* have been demonstrated to colonize the respiratory tract. Competition with a combination of *Lactobacillus* species reduced GAS adherence to host cells most efficiently. The effector molecules released from *Lactobacillus* strains affecting the virulence phenotypes of pathogens is believed to be useful in the development of a new generation of therapeutics. *S. pyogenes* produces a wide array of virulence factors, enabling it to adhere, invade, and spread within the human host. One aspect of the present invention relates to the impairment or deletion of such virulence factors to provide a bacteria that may competitively compete with other strains, thus providing a way for a person to populate their oral cavity with a less infectious bacteria and thus, avoid sore throats.

Adherence of *Streptococcus pyogenes* to human epithelial pharangeal and oral mucosal cells can be inhibited by oligosaccharides, preferably associated with one or more strips as described herein prior to placement of the stirps in a person's throat. In U.S. Pat. Nos. 5,002,759 and 5,095,106, which are incorporated by reference, oligosaccharide compositions and methods are described that inhibit the adhesion of *S. pyogenes* on pharyngeal and oral mucosa. The inhibitory activity of these oligosaccharides can be substantially enhanced by coupling them with a carrier to make glycoconjugates. Thus, in various embodiments of the present invention, in addition to the structural features of the strips as disclosed herein that have anti-bacterial properties, preferred embodiments also include one or both of oligosaccharides and glycoconjugates. Oligosaccharides may be selected from the group consisting of A-tetrasaccharide, B'-sialyllactose, lacto-N-tetraose, B-trisaccharide, fucosyllactose, lacto-N-neotetraose and gangliotetraose. Preferably the oligosaccharide is conjugated to human serum albumin or bovine serum albumin. Specific examples further include the oligasaccharide—conjugates Gal 1-3 Gal N-acetyl-Human Serum Albumin, lacto-N-fucopentaose 1,1,1-Human Serum Albumin, Galbeta 1-4 galactose N-acetyl beta 1-0-para amino phenyl Human Serum Albumin.

Bioadhesion, in particular mucoadhesion, has been of interest for the development of controlled drug delivery systems to improve buccal and oral administration of drugs. Carboxylated polymers, such as poly(acrylic acid) and crosslinked poly(acrylic acid), are known to be effective as mucoadhesives (hereinafter bioadhesive compositions). Various bioadhesive compositions comprising poly(acrylic acid) are described, e.g., in WO 98/22097; EP 410,696; U.S. Pat. Nos. 5,643,603; 4,915,948; 5,895,804; 20070218114 to Duggan; and U.S. Pat. No. 6,284,235, all of which are incorporated herein by this reference for particular embodiments of the invention.

Other embodiments are directed to an oral strip having a preloaded population of bacteria residing thereon (or that can be cultured on the strip after triggering the growth of the bacteria pre-placed thereon) such that there is competitive inhibition of other bacteria, namely *S. pyogenes*, such that sore throats are avoided or at least lessened in severity.

The strips of the present invention may be configured for inter-oral administration and may contain either an anti-bacterial surface to which few, if any bacteria attach, or alternative strips have pre-determined populations of "friendly bacteria" thereon, such that the surface area for *S. pyogenes* to grow is thus limited, effecting the prevention of a sore throat and therefore providing a method for the preparation thereof and use thereof in alleviating throat conditions or throat disorders. In yet other embodiments, thin films are adapted for attachment to the mucosal membrane, in particular to the back region of a person's throat where bacteria reside, and in particular bacteria that cause disease and result in a person experiencing a sore throat, with such thin films having an effective amount of xylitol. It has been found that bacterial resistance is one of the main problems in controlling recurrent infections and the improper use of antibiotics has permitted many microorganisms to adapt and become resistant to treatment. A better way of controlling this phenomenon is through bypassing the bacteria's adaptive qualities altogether.

The microbiota prevents colonization with pathogenic bacteria and represents an important first line of defense. Mechanisms describing the probiotic effects of *Lactobacillus* strains include upregulation of mucin production in the host cells, interference with host pattern recognition receptors, competition for essential metabolites, production of antibacterial molecules, and co-aggregation between the bacteria of the microbiota and invading pathogenic bacteria, leading to interference with pathogen adherence to host cells. This later ability to coaggregate with *S. pyogenes* (using certain strains of *lactobacillus*) forms one embodiment of the present invention and is responsible for the ability to thwart sore throat to progress in a human when a strip of the present invention is applied at a time prior to full *S. pyogenes* adherence to mucosal tissue. *Lactobacillus* components mediating adherence inhibition are known by those of skill in the art and may be employed in the context of strips as described herein so as to inhibit the adherence of different pathogens, but especially *S. pyogenes* in the context of sore throat infections. Colonization with *Lactobacillus* species impairs GAS pathogenicity at different stages of infection, both by reducing the adherence at earlier stages and by affecting the viability after prolonged incubation and attenuating the hemolytic activity. In other embodiments, phytochemicals are employed as alternatives to the classical antibiotics currently used for the treatment of streptococcal infections. Preferred phytochemicals demonstrate direct bactericidal or bacteriostatic effects, such as: (i) prevention of bacterial adherence to mucosal surfaces of the pharynx, skin, and teeth surface; (ii) inhibition of glycolytic enzymes and pH drop; (iii) reduction of biofilm and plaque formation; and (iv) cell surface hydrophobicity. The use of other factors, such as dispersin B, or glycoside hydrolase produced by the periodontopathogen *A. actinomycetemcomitans*, may be employed to inhibit biofilm formation and disperse biofilms formed by several bacterial species.

The present invention includes a method that reduces the duration, frequency, or severity of sore throat disease. In certain embodiments, strips of the present invention provide a barrier-forming surface overlying the mucosa and preferably having the anti-bacterial surface such that *S. pyogenes* populations on the mucosal surface is thwarted and such surface is either antimicrobial due to its physical conformation and/or is active to kill or neutralize microorganisms in the oral cavity.

The naturally occurring sugar Xylitol is a natural sweetener and has an anti-adherence property that is believed to interfere with many microorganisms ability to cling to cell tissues. As bacterial infection occurs when bacteria adheres to tissues in a manner that permits colonization and growth, the use of xylitol is believed to prevent this action and in the process, stave off bacterial infection. One problem with prior art administrations of xylitol has been to provide xylitol in effective concentrations, in the proper place (e.g. in contact with particular tissue), and for an extended period time so as to achieve its anti-bacterial abilities. Sprays and merely chewing gum containing xylitol have shown some benefits in terms of dental cavity prevention and in washing of nasal tissues. But the present invention is effective in isolating the particular tissue most at risk of bacterial infection—the back of one's throat—and focuses an effective concentration of xylitol (as well as the many other agents and bacteria as described herein) on such tissue for an appropriate and effective period of time so as to reduce the number of undesired bacteria that would otherwise exist on the tissue of one's throat. Because the bacteria are not allowed to infect, antibiotics are not needed in certain embodiments of the present invention.

While not bound by theory, it is believed that xylitol disperses and disrupts biofilms and thus, in addition to its anti-adherence property, xylitol is able to help in the treatment of diseases where bacteria and other microorganisms are the causative agents. It is further believed that xylitol is effective in dispersing yeast-born bacterial microorganisms and in controlling their growth. It is also speculated that xylitol is a glucose competitor that is able to inhibit glycolysis.

Because of its five-carbon sugar alcohol structure, xylitol is unsuitable as a source of energy for most oral microorganisms, such as *Streptococcus mutans*. Yet, most *S. mutans* strains are, via the fructose phospho-transferase system, able to transport xylitol into the cell, where it is phosphorylated into xylitol-5-phosphate, which then has to be expelled from the cell. This metabolically futile xylitol cycle consumes energy stores of the cell and is thought to be responsible for the inhibition of the growth of *S. mutans* observed both in vitro and in vivo when exposed to xylitol. Because the bacteria are not killed, resistance is not as big a problem. Use of the strips of the present invention are suited for the treatment of appropriate infections and reduces the need for second and third generation antibiotics. In certain embodiments, the re-population of the mouth with a population of bacteria that are considered to be more healthy than infectious bacteria is one aspect of many embodiments of the present invention. Due to its crystalline structure, i.e., distinct single crystal, definitive form, and very dense nature, when added to a strip of the present invention, aqueous crystallized xylitol does not "dry" the strip out. Xylitol is a pentitol and is used not only as a sweetener but also as a platform chemical for the production of industrially important chemicals. Oral bacteria thrive on certain carbohydrate molecules such as sucrose, glucose, fructose and other sugars but when they ingest xylitol, they cease proliferating and cease to adhere to human tissues. Delivering xylitol via the strips of the present invention also provides other benefits, such as remineralization of teeth and reduction of plaque and halitosis by stimulating saliva flow.

The present invention provides for a strip that can be adhered to the mucosal membrane and preferably to a particular upper mouth portion of a person's mouth that contains the bacteria that causes bad breath, promotes diseases, etc. The strip, when it dissolves, releases xylitol or a similar polyol. And there is a need to slow the rate of dissolution to maintain therapeutic levels of xylitol or other polyol in the fluids of the oral cavity over longer periods of time and this is achieved by the strips of the present invention. Many causes lead to congestion and irritation of the exposed surfaces of the respiratory tract, especially the throat. The use of strips of the present invention, especially those formulated with a particular concentration of saline and with xylitol, are believed to significantly reduce and decrease snoring. Certain formulations of the strip, especially those that include particular saline concentrations, are believed to pull fluid from the mucosa and at the same time, flushes out germs, contaminants, and pollutants (pollen/dust/sand/soot/smoke, etc.) from the mucus membranes. For example, in particular embodiments, strips that are adapted to be adhered to the mucosal membrane include a preservative free hypertonic saline at 2.3% to and including 2.7% w/v (preferably 2.4% to and including 2.6% w/v) salt is effective.

In one aspect, the invention is a strip having polyol molecules, particularly xylitol, with a reduced rate of dissolution in saliva and that preferably dissolves much more slowly than substantially pure (greater than or equal to 98%) xylitol. Preferably, strips do not substantially swell when exposed to water. Strips may be formed by melting the polyol and then cooling them until the polyol molecules crystallize or by pressing powders of polyol crystals into a strip. In certain embodiments, the dissolution time of the strip in a human mouth is, on average, more than 25 minutes more preferably, more than 1 hour, and most preferably, more than about 3 hours. To achieve slow release of polyol molecules, the strips may be formed with low water levels so that the polyol, preferably xylitol, particles do not dissolve readily or quickly. Thus, some embodiments include fine grains of xylitol with 2.5%-6% carboxymethylcellulose (CMC) (by weight relative to the xylitol) incorporated into strips with insignificant amounts of water. The laryngeal/pharyngeal cavity is lined with a mucosa the essential component of which is the epithelium. The epithelium is the interface between the human body and ingested substances and forms a complex physicochemical barrier which, supplemented by the mucociliary apparatus, constitutes the first defense against pathogens. Mucus covers the epithelium and provides an additional protection for the mucosa, in which it forms a semi-permeable barrier that allows the exchange of nutrients, water and gases but keeps out pathogenic germs. Mucus is a viscoelastic gel of complex composition which is continuously secreted by intraepithelial cells and salivary glands. The main components of mucus are mucins, large and strongly charged glycoproteins which form the structural framework of the mucosal barrier by cross-linking. Strips of the present invention, in certain embodiments, are designed and adapted to adhere to the mucosal membranes (preferably buccal but also could be vaginal, rectal, etc.) to provide a slow release of effective amounts of polyols, and preferably xylitol, for a period of time in contact with such membranes for over about 1 hour, more preferably over about 3 hours and even over 5 or more hours. In one embodiment, the invention is directed to a thin film composition for administering an active ingredient comprising a film layer, wherein the film layer had an anti-bacterial agent consisting essentially of xylitol; wherein said thin film is adhesive to a mucosal membrane and is dissolvable over a period of no less than about 2 hours. Preferably the film strip weighs about 10 to 80 mg per strip and includes xylitol having a particle size of about 10 to 400 mesh.

Still other embodiments include combinations of various herbal and sugar components, such as xylitol and tomatidine in a mucosal adhesive strip that achieves the combined functionality of those particular ingredients, e.g. reducing bacteria and facilitating muscle tissue health.

To provide necessary and sufficient written disclosure and enablement of the various embodiments of the present invention, the following references are incorporated by reference in their entireties: U.S. Pat. No. 9,017,718 to Tan; 20140065218 to Lang et. al.; U.S. Pat. Nos. 6,599,883; 8,383,201; 5,158,789; 2007/0218114 to Sorousch; 2004/0136923 to Davidson; U.S. Pat. No. 8,999,372 to Davidson; 2009/0196907 to Bunick; 2009/0196908 to Lee; 2003/0124178 to Haley; 2007/0293587 to Haley; 2010/0285098 to Haley; 2006/0204591 to Burrell; U.S. Pat. No. 7,087,249 to Burrelll; U.S. Pat. No. 6,210,699 to Acharya; U.S. Pat. No. 8,865,211 to Tzannis; 2014/0199266 to Park; U.S. Pat. No. 6,599,883 to Romeo; PCT/US2008/080362 to Dussia; 2007/0218114 to Duggan; 2004/0136923 to Davidson; 2011/0142942 to Schobel; 2004/0120991 to Gardner et al.; Fuchs et al. U.S. Pat. No. 4,136,162; 2004/0136923 to Davidson; U.S. Pat. No. 4,163,777 to Mitra; U.S. Pat. No. 5,002,970 to Eby, III; 2004/0096569 to Barkalow et al.; 2006/0035008 to Virgallito et al.; 2003/0031737 to Rosenbloom; U.S. Pat. No. 6,919,373 to Lam et al.; 2005/0196358 to Georglades et al.; U.S. Pat. No. 3,832,460 to Kosti; 2002/002057 to Battey et al.; 2004/0228804 to Jones, et al.; U.S. Pat. No. 6,054,143 to Jones; U.S. Pat. No. 5,719,196 to Uhari; 2015/0150792 to Klingman; 2014/0333003 to Allen; 2014/0271867 to Myers; 2014/0356460 to Lutin; 2015/0038594 to Borges; U.S. Pat. No. 6,139,861 to Friedman and US pat. Publication No. 20140065218.

Another aspect of the certain embodiments of the present invention is directed to a thin film mucosal layered strip that includes several layers, and in one particular embodiment, at least four layers, with a first layer comprising an odor impervious material, a second layer that comprises at least one encapsulated solvent, a third layer having a solvent absorbent material, and a fourth layer comprising an adhesive, wherein the solvent is encapsulated in a frangible enclosure and is present in an amount of at least about 0.5 ml. The solvent can include various compositions and chemicals or natural compounds, but include breath freshening agents, lubricants, xylitol, medicines, crosslinking agents, etc. Certain embodiments of such a layered strip include a color change indicator, preferably as part of one of the second layer and the third layer. The strip may also include one or more odor reducing agents.

Still other embodiments include the use of a strip that has at least one compartment or encapsulation area where a desired agent is provided that can be purposefully released at a given time while in the oral cavity. For example, provision of an analgesic encapsulated in a frangible shell that is associated with the strip can be used to provide a person with the ability to pop such shell and release analgesic when the pain associated with a sore throat develops. More importantly, treatment agents can be encapsulated in such strips, such that antibiotics or co aggregation agents or LAB, etc. can be encapsulated in a manner that they can be released into the oral cavity at a time when the person so desires and/or when the strip dissolves to a certain extent, e.g. when the walls of the encapsulating shell is worn thin enough to fracture to release the agent(s). The manner in which a capsule can be fractured in order to release its solvent contents is variable and will be understood by those of skill in the art. Preferably, the capsule is constructed in a manner that it is sufficiently robust such that mere transport and packaging of the strips containing such capsules does not cause any leakage or breakage of such capsules. Instead, the design of capsules is such that they are frangible with a considerable amount of force being directly applied thereto once the strips are placed on a particular mucosal surface, such as on the soft palette of a human, such that the person's tongue, when pressing against such capsule, can cause it to fracture to release the contents of the capsule. In other embodiments, two or more different materials may be released (such as a xylitol containing solvent and a color change agent) and a divider may be employed that may comprise a membrane having one or more zones of weakness, such as a declivity or score line, such that when a hollow body comprising the encapsulated structure is manipulated, such as being bent, pressed, crushed, flexed, or compressed along a zone of weakness, an opening is created in the divider, permitting the contents of a first compartment and a second compartment to mix. Such a hollow body preferably has an opening at a first end, and a frangible seal that closes the opening to retain the contents housed in the hollow body. In one embodiment, the frangible seal comprises a thin membrane, for example, thin films of plastic or biodegradable material. In other embodiments, an absorbent material is also employed to retain the released solvent in a particular location for a desired period of time, which may include a semi-porous material, such as a sponge. When the frangible seal is broken, the contents of the hollow body are released into the absorbent material. The hollow interior of the solvent containing member may define a reservoir for containing a liquid composition, such as the solvent, color change material, etc.

Preferably, a frangible seal is provided that is liquid-tight prior to use of the strip. The frangible seal is designed to preferably be weaker than the seal at one end, thus when the solvent containing capsule is manipulated, for example by squeezing, tongue manipulation, etc. it causes the frangible seal to be broken, permitting the solvent or other liquid material in the reservoir to flow out. A number and variety of desired substances may be employed in association with such an absorbent layer via employment of a frangible capsule that can contain such substance, especially in association with an adhesive portion of the strip so that the substance can be administered to the desired site. Thus, such frangible capsules of the strip can be used in association with a capsule containing a wound healing substance, or a pain killer, an allergesic, a medicine, a growth promoting material, a muscle treatment gel, deodorant, etc. such that the affected area can be covered and then at a desired time, the capsule can be broken to release the desired pre-packaged substance or combination of substances. In one particular embodiment, the use of a capsule is employed that can contain more than one substance separated by frangible structures such that a combination of substances can be delivered in a desired sequence and in a particular position on a surface, such as a person's mucosal membrane or skin, so that the purposeful combination of such substances can be achieved in an easy fashion. The strips of the present invention, by virtue of their encapsulated frangible structures, whether or not associated with absorbent materials and barriers find various uses that are accomplished in an easy, cost effective manner and enables one to carry the devices with them for use outside of medical clinics, etc. In certain embodiments, the breaking of one or more encapsulations that contain an anti-odor component, such as a breath freshener, a cyclodetrin component to mask or eliminate certain odors, can be used for various mucosal adhesive encapsulated structures.

One aspect of the present invention is directed to a microorganism that binds to *Streptococcus pyogenes*, preferably such microorganism being a lactic acid bacterium. In an especially preferred embodiment, the microorganism or the analog, fragment, derivative, mutant or combination thereof, belongs to the *Lactobacillus* genus and in other preferred embodiments, the microorganism or analog, fragment, derivative, mutant or combination thereof does not have the ability to coaggregate with commensal microorganisms of the mucous membranes. Such a microorganism is preferably selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum, Lactobacillus ingluviei* or analogs, derivatives, fragments or mutants thereof.

Preferred products for application of various compounds and substances of the present invention include, in addition to the preferred use of strips as described herein, toothpaste, mouth washes, gargle solutions, nose sprays, mouth sprays, throat sprays, chewing gum, hydrogel, creams, etc.

The preferred composition is for topical prophylaxis or treatment of microbial diseases of inflammatory diseases of the oral cavity. It is preferably for use in prevention or treatment of microbial diseases of the oral cavity but can also be used for topical prevention or treatment of microbial diseases or inflammatory diseases, preferably microbial diseases or inflammatory diseases of the skin. In some embodiments, the composition may be used to produce an antimicrobial additive for topical treatment of inflammations in the oropharyngeal space and may be used prophylactically and may be applied orally, sublingually or buccally.

The preferred lactic acid bacteria coaggregates specifically with the pathogenic bacteria *Streptococcus pyogenes*. As adhesion is an essential first step in bacterial pathogenesis, one aspect of the present invention is focused on adhesion as a way to prevent sore throat infections. In various embodiments, *S. pyogenes* is coaggregated in the oral cavity, so that binding to epithelial cells cannot take place from the beginning. In other embodiments, the coaggregation is accomplished due to the provision of a strip that adheres to the top most portion of a person's mouth where certain bacteria are provided to coaggregate with *S. pyogenes*. Typically, the resulting cell aggregates are swallowed with saliva and the *Streptococcus pyogenes* cells are killed during gastrointestinal passage. Certain preferred bacteria used in the present invention are found on the skin flora and are able to bind to or coaggregate with the pathogenic bacterium *Streptococcus pyogenes*. Preferred lactic acid bacteria coaggregate with *Streptococcus pyogenes* or have adhesive properties with respect to these bacteria. The coaggregation of *Streptococcus pyogenes*, is not inhibited either in saliva or in the presence of sugars.

It is known that coaggregation processes are generally inhibited by high sugar concentrations, but certain lactic acid bacteria will coaggregate with *Streptococcus pyogenes*, even at high sugar concentrations such as those occurring in saliva.

Those skilled in the art are aware that *Streptococcus pyogenes* is also known as a pathogenic wound organism, so it is especially advantageous that the coaggregation capability of the preferred microorganisms is not limited to the oral cavity but instead can also be applied to areas of the skin. Preferred microorganisms can also be used on skin, where it will also coaggregate with *Streptococcus pyogenes*.

Certain bacteria employed herein specifically coaggregate the pathogenic bacterium *Streptococcus pyogenes*, but do not bind any other commensal microorganisms. In particular embodiments, particular cultures are employed and a CRISPR-Cas system is used to modify such cultures to remove certain virulence factors and/or to promote their survival in the oral cavity. The CRISPR-Cas system is preferably employed to excise the virulence factors of one or more of the following bacteria: *Lactobacillus lactis, Lactobacillus helveticus, Lactobacillus jensenii, Lactobacillus acidophilus, Lactobacillus bulgaricus, Lactobacillus amy-*

*lovorus, Lactobacillus delbrueckii, Lactobacillus casei, Lactobacillus crispatus, Lactobacillus gasseri, Lactobacillus johnsonii, Lactobacillus paracasei, Lactobacillus pentoses, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermen turn, Lactobacillus reuteri, Lactobacillus viridescens, Bifidobacterium bifidum, Lactobacillus ingluviei* and preferably selected from the group comprising the following microorganisms deposited with the German Collection for Microorganisms and Cell Cultures where they are numbered as DSM 25972, DSM 25987, DSM 25988, DSM 25989, DSM 25973 and have been in accordance with the Budapest Treaty regarding International Recognition of the Deposition of Microorganisms for the purpose of patent deposition.

In a preferred embodiment of the invention, strips containing effective amounts of these bacteria are provided that are attached to the soft palate region of a person's mouth, thus providing a prophylactic product to prevent the advancement of sore throat. In other preferred embodiments, an extract of cranberries is provided as it is believed that coaggregation of *Streptococcus pyogenes* is substantially more efficient when a solution of cranberries is present. Through the formation of coaggregates, *Streptococcus pyogenes* is prevented from colonizing and invading cells of the throat area in particular. The *Streptococcus pyogenes* cells, in particular their cell surface, are believed to be masked by the lactic acid bacteria, in particular *lactobacillus* cells, so that the *Streptococcus pyogenes* cells are preferentially no longer able to bind to the epithelial cells of the skin and mucous membranes. Thus, one aspect of the present inventon is directed to the competitive inhibition of *S. pyogenes* growth in an individual's mouth by the administration of certain *Lactobacillus microbes* to defeat further adhesion and disease progression. Inflammation reactions are prevented by the hindered binding of *Streptococcus pyogenes* to the epithelial cells of the skin and mucous membranes.

The prevention of the binding of *Streptococcus pyogenes* at a very early stage of a sore throat to epithelial cells and to promote purposeful coaggregation of *Streptococcus pyogenes* in the oral cavity is believed to provide an effective non-antibiotic way to defeat the tremendous pain and sickness associated with this long felt but unsolved health problem.

The coaggregatoin products can be removed mechanically, for example, by rinsing them off via a mouth wash, etc. so that the number of pathogenic microorganisms is reduced.

Another property of the lactic acid bacteria according to the invention is the capability to inhibit binding to host cells by *Streptococcus pyogenes* in that these cells, which are already present in planktonic form, are specifically coaggregated and then washed away as aggregates. These pathogenic bacteria can no longer colonize and invade biological surfaces due to this coaggregation and therefore they also cannot cause any diseases. Therefore in the sense of the present invention, the phrase "inhibiting the binding to host cells (oropharyngeal cells) by *Streptococcus pyogenes*" is to be understood to refer in particular to the property of the lactic acid bacteria according to the invention to interact with *Streptococcus pyogenes*, i.e., to bind to them or otherwise influence them in such a way that they can no longer bind to oropharyngeal cells.

In certain embodiments, CRISPR-Cas is used to modify *S. pyogenes* so that it lacks the ability to adhere to epithelial cells and also to be able to coaggregate to *lactobacillus* species in a substantially greater degree than wild type *S. pyogenes*. In such a manner, one achieves high coaggregation activity in human saliva and the resulting aggregates of *Streptococcus pyogenes* are stable and thus can be removed by simple rinsing or swallowing. In particular, the coaggregation efficiency can be increased significantly in the presence of cofactors (EDTA, MgCl2, CaCl2, SDS). To determine which particular *lactobacillus* species can be employed, one of skill in the art will appreciate how to determine if a particular *lactobacillus* strain is able to coaggregate with one or more of *S. mutans; S. mitis, S. salivarius, S. gordonii* and *S. sanguis*. If it cannot, then such *lactobacillus* is a candidate for a coaggregation bacteria with *S. pyogenes*. Coaggregation, the specific recognition and adherence of different microbial species, is thought to enhance biofilm formation. Nasopharyngeal bacteria belonging to the human opportunistic pathogen archetype showed the least number of coaggregations. Thus, in certain embodiments, the present invention is directed to employing CRIPR-Cas systems to enhance the ability of pathogenic organisms, in particular *S. pyogenes*, to coaggregate with other bacteria, preferably other *lactobacillus* bacteria, and more preferably those described herein with particular deposit information.

Thus, several aspects of the present invention are directed to the use of particular LAB to inhibit or modulate one or more of adhesion, invasion and virulence expression to facilitate clearance of a pathogen, and in particular to advance coaggregation with *S. pyogenes* without necessarily killing such pathogen.

Other aspects are directed to the pre-colonization of a person's oral cavity with preferred LAB to reduce adhesion of epithelial cells to pathogenic microbes, and especially *S. pyogenes*. It is further believed that use of LAB having superior adherent properties (as it relates to adherence to epithelial cells) is effective in competitively inhibiting *S. pyogenes* infection and that such LAB also displace pathogens binding to epithelial tissues. Thus, effective colonization of LAB to a person's throat tissues, such as via the use of the strips as described herein (especially those impregnated with LAB and an effective growth media on the strip for those LAB, is an effective way to achieve desired colonization. The further use of strips having antibacterial surfaces such that the strips discourage populations of *S. pyogenes* achieving critical numbers to promote a continuance of sore throat is yet another aspect of the present invention. Again, it believed that the LAB coaggregation with *S. pyogenes* is one of the principal reasons the progression of sore throat does not occur when effective amounts of LB are administered to one's throat. The strip embodiments of the present invention are believed to be very effective in providing such LAB populations in a continued format as the regular continued swallowing of LAB otherwise could rid the oval cavity of LAB that would otherwise be present to coaggregate with *S. pyogenes*. By having the LAB effectively present on tissue that would otherwise be adhered to by *S. pyogenes*, the avoidance of major sore throat infections is achieved. Thus, coaggregation of lactobacilli with pathogens is one mechanism that can explain adhesion inhibition.

Other LAB that may be employed in various embodiments include the following: *Lactobacillus slaivarius* CICC 23174; *Lactobacillus plantarum* CGMCC 1.557, *Lactobacillus rhamnosus* ATCC 53103, and *Lactobacillus acidophilus* ATCC 4356. In other particular embodiments, the use of *S. oralis* and *S. salivarius* may be used in combination to inhibit growth of *S. pyogenes*, with speculation being that *S. salivarius* may achive this feat via bacteriocin secretion.

Epithelial cells are believed to be protected from infection by *S. pyogenes* when a biofilm containing *S. oralis* and *S. salivarius* is applied, with *S. pyogenes* unable to adhere to such tissue, thus the individual is protected from the adherence, internalization, and cytotoxic effects of a sore throat.

Other aspects of the present invention involve the elimination of or reduction of the presence of certain bacteria that appear to enhance the ability of *S. pyogenes* to adhere to epithelial tissues, one of such bacteria being *Moraxella catarrhalis*. Thus, an effective reduction of *Moraxella catarrhalis* by various means, such as by an antibiotic, can be used to reduce the chances of infection with *S. pyogenes*.

Popping capsules when one feels that their throat feels like it is getting sore is one aspect of the present invention. The timeliness of being able to address an imminent cellular interaction by providing medications or beneficial agents directly to the tissue at issue by merely having one's tongue cause a frangible vesicle, encapsulation, etc. to release a desired agent to contact with the tissue, is a novel way in which to effectively stop a biological process before it progresses to a later stage, at which point the desired effect of the agent may not be efficacious. For example, when one believes that they are feeling the onset of a sore throat, often described as a tickling of their throat, such individual can apply one of the strips of the present invention directly to the roof of their mouth—employing the mucosal adhesive nature of such strip. The strip may also include encapsulated pockets filled with beneficial agents so that breakage of such capsules, preferably by action of one's tongue pressing against the capsule into the roof of the person's mouth, causes the capsule to break, thus releasing the agents inside. Such agents can include, for example, beneficial bacteria, saline solutions of various strengths, antibiotics, co-aggregation agents, etc.

In still other embodiments, employment of technology described in U.S. Pat. No. 9,131,884 to Holmes is employed to achieve desired further steps to address communication of biological disease status to a third party and in particular, the presence of a sore throat in a human. For example, in certain embodiments, a medical device is associated with a mucosal strip that comprises a microarray having a bioactive agent capable of interacting with a disease marker biological analyte and a reservoir having at least one therapeutic agent, with the device able to release the therapeutic agent(s) from the medical device. In certain embodiments, at least two microchips with a microarray scanning device adapted to obtain physical parameter data of an interaction between the disease marker biological analyte and the bioactive agent is employed. A biometric recognition device is configured to compare the physical parameter data with an analyte interaction profile. The therapeutic agent releasing device controls the release of the therapeutic agent from the reservoir. The interface device facilitates communications between the microarray scanning device, biometric recognition device and the therapeutic agent releasing device. An energy source to power the medical device can take several forms, including biologically activated batteries that are preferably associated with the strip.

Thus, in certain embodiments, sugar is used as a source of energy, notably glucose that is converted into different sugars via an enzymatic cascade to provide necessary energy to create an electrochemical gradient. This, in turn, is used to power an enzyme that synthesizes adenosine triphosphate (ATP). In contrast to natural catabolic pathways for cellular glucose oxidation, a preferred embodiment does not rely on ATP as an energy carrier. Instead, two redox enzymes oxidize glucose, generating reduced nicotinamide adenine dinucleotide (NADH) as the sugar is broken down. Another series of enzymes (as many as ten additional enzymes) further breakdown the sugars and feed them back to the redox enzymes to produce more NADH, with water and carbon dioxide being the only by-products. NADH is a reducing agent and acts as an electron shuttle that carries electrons in living cells from one molecule to another. NADH first transfers the electrons stripped from the glucose to a mediator with the help of an enzyme. The mediator then delivers these electrons to the battery's electrode, rendering it available to power an electronic device. Such a battery mimics the way a living cell transfers electrons from one molecule to another to generate power, it runs on renewable sugars, and has a high-energy storage density, rechargable providing an additional sugar solution. Malodextrin—a polymer made up of glucose subunits—may be employed together with particular different enzymes able to strip electrons from a single glucose molecule, thus harnessing the generated energy to power an electrical device. The use of such device, incorporated into the strip as otherwise described herein, but especially those that have at least two of the following characteristics (LAB eluting structures; CRISPR-Cas system modified LAB to enhance coaggregation with *S. pyogenes*; inclusion of an anti-bacterial structural surface (see FIG. 2), etc.) can then be used to communicate the status of a person's health to a third party due to the energy producing system as described herein.

In various embodiments of the present invention, bacterial species are able to use various energy sources, including light and diverse organic and inorganic chemicals, for growth and metabolism. These energy sources are used to produce an electrochemical gradient that provides an electron donor for metabolism and allows maintenance of a membrane potential and proton motive force. The energetics of living systems are driven by electron transfer processes in which electrons are transferred from a substrate, which is thereby oxidized, to a final electron acceptor, which is thereby reduced. In certain embodiments, it is possible to control metabolism by linking biochemical processes to an external electrochemical system, with such linking of biochemical and electrochemical systems permitting the use of electricity as a source of electrons for biotransformation reactions. A reversible biochemical-electrochemical link allows for conversion of microbial metabolic and/or enzyme catalytic energy into electricity.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

What is claimed is:

1. A bioadhesive strip for treating sore throat in a human being, comprising: a solid strip having a first and second side, said first side having a surface comprising a pattern defined by a plurality of spaced apart features each having at least one microscale dimension and having at least one neighboring feature having a substantially different geometry, wherein an average spacing between adjacent ones of said features is between 0.5 and 5 microns in at least a portion of said surface, the first side having a bioadhesive that is adapted to bind to a mucosal membrane for at least 1 hour while inside a person's mouth, wherein said strip is sized to extend over a majority of the soft palate, and wherein said strip includes one of an analgesic, and a lactic acid bacteria that coaggregates with *S. pyogenes*, and wherein a clustered regularly interspaced short palindromic repeats (CRISPR) CRISPR associated protein (Cas) system or a CRISPR from *Prevotella* and *Francisella* 1 (Cpf1) system is employed to silence or to delete at least one virulence factor of *S. pyogenes*.

2. The strip of claim 1, wherein said strip includes at least one polymer selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

3. The strip of claim 1 wherein said strip has an analgesic encapsulated inside a frangible capsule that may be broken by a person pressing against said strip with the person's tongue.

4. The strip of claim 1 wherein said strip is non-dissolvable in a person's mouth.

5. The strip of claim 1 wherein said strip is dissolvable in a person's mouth within a period of 3 hours.

6. The strip of claim 1, wherein the strip comprises at least one encapsulated feature.

7. The strip of claim 1, wherein said strip further includes at least 200 mg of xylitol.

8. The strip as set forth in claim 1, wherein said strip comprises *Prevotella* bacteria.

9. A bioadhesive solid strip for treating sore throat in a human being, comprising: at least one surface of said strip having a pattern defined by a plurality of spaced apart features each having at least one microscale dimension and having at least one neighboring feature having a substantially different geometry, wherein an average spacing between adjacent ones of said features is between 0.5 and 5 microns in at least a portion of said at least one surface, said strip having a first and second side, the first side having a bioadhesive that is adapted to bind to a mucosal membrane for at least 1 hour while inside a person's mouth, said strip having a length dimension of between 0.5 and 2 cm; a surface area of between 0.25-1.5 square inches; a weight of at least 30 mg; and includes bacteria modified by a CRISPR-Cas or Cfp1 system.

10. The strip of claim 9, wherein the strip comprises *S. pyogenes* modified by a CRISPR-Cas system to reduce one or more virulence factors.

11. The strip of claim 1, wherein the strip is dissolvable in a person's mouth after one hour.

12. The strip of claim 9, wherein the strip comprises *S. pyogenes* that have been modified to remove or disable one or more virulence factors and wherein the *S. pyogenes* is encapsulated on the strip within a pouch or pocket.

13. The strip of claim 9, wherein the strip includes *S. pyogenes* that have been modified to render ineffective virulence factors in a manner effective to avoid sore throat progression.

14. The strip of claim 9, wherein the bacteria modified by a CRISPR-Cas or Cfp1 system are lactic acid bacteria that coaggregate with *S. pyogenes*.

15. The strip of claim 9, wherein said strip reduces the adhesion of *S. pyogenes* to an epithelial tissue of a person.

16. The strip of claim 9, wherein the strip has a thickness of between 100-400 microns thick and includes one of bacterial and helminth components.

17. The strip of claim 9, wherein said strip has an analgesic encapsulated inside a frangible capsule that may be broken by a person pressing against said strip with the person's tongue.

* * * * *